US011931531B2

(12) United States Patent
Scherich et al.

(10) Patent No.: US 11,931,531 B2
(45) Date of Patent: Mar. 19, 2024

(54) PLUNGER-BASED DELIVERY DEVICE TO FACILITATE VASCULAR ACCESS

(71) Applicant: Becton, Dickinson and Company, Franklin Lakes, NJ (US)

(72) Inventors: Megan Scherich, Salt Lake City, UT (US); Jonathan Karl Burkholz, Salt Lake City, UT (US); Curtis H. Blanchard, Riverton, UT (US); Weston F. Harding, Lehi, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 293 days.

(21) Appl. No.: 17/146,400

(22) Filed: Jan. 11, 2021

(65) Prior Publication Data

US 2021/0228842 A1 Jul. 29, 2021

Related U.S. Application Data

(60) Provisional application No. 62/965,641, filed on Jan. 24, 2020.

(51) Int. Cl.
*A61M 25/06* (2006.01)
*A61M 5/31* (2006.01)
(Continued)

(52) U.S. Cl.
CPC ........ *A61M 25/0606* (2013.01); *A61M 25/09* (2013.01); *A61M 5/3129* (2013.01);
(Continued)

(58) Field of Classification Search
CPC ........ A61B 5/150198; A61B 5/150206; A61B 5/150236; A61B 5/150244; A61B 5/150374; A61B 5/150534; A61B 5/150564; A61M 2025/0019; A61M 2025/0177; A61M 2025/09116; A61M 25/0017; A61M 25/09; A61M 25/09041;
(Continued)

(56) References Cited

U.S. PATENT DOCUMENTS 1,612,996 A * 1/1927 Waagbo .................... G01N 1/14
222/386
3,216,616 A * 11/1965 Blankenship, Jr. ..........................
A61M 5/31596
D24/114
(Continued)

FOREIGN PATENT DOCUMENTS

JP 2000014791 1/2000
JP 2000014791 A * 1/2000 ......... A61B 5/15003

*Primary Examiner* — Jason E Flick
*Assistant Examiner* — Adam J. Cermak
(74) *Attorney, Agent, or Firm* — The Webb Law Firm

(57) ABSTRACT

A delivery device for delivering an instrument into a catheter assembly may include a syringe, which may include a barrel and a plunger movable within the barrel. The plunger may include a handle and a stopper coupled to a distal end of the handle. The stopper may include a channel. The delivery device may include a guidewire disposed within the barrel and extending through the channel. In response to depression of the plunger, the guidewire may move through the channel and a first end of the guidewire may be advanced in the distal direction. A second end of the guidewire may be fixed.

19 Claims, 17 Drawing Sheets

(51) Int. Cl.
*A61M 5/315* (2006.01)
*A61M 25/01* (2006.01)
*A61M 25/09* (2006.01)

(52) U.S. Cl.
CPC . *A61M 5/31511* (2013.01); *A61M 2025/0177* (2013.01); *A61M 2025/09116* (2013.01); *A61M 2205/19* (2013.01)

(58) Field of Classification Search
CPC .. A61M 2005/2477; A61M 2005/3143; A61M 2005/3123; A61M 5/31511; A61M 5/3129
See application file for complete search history.

(56) References Cited

U.S. PATENT DOCUMENTS

| | | | | |
|---|---|---|---|---|
| 3,566,859 A * | 3/1971 | Schwartz | ......... | A61B 5/150519 604/82 |
| 4,464,171 A * | 8/1984 | Garwin | ........... | A61M 25/09041 604/510 |
| 4,525,157 A * | 6/1985 | Vaillancourt | ...... | A61M 25/0111 604/165.01 |
| 4,615,341 A * | 10/1986 | Marzolf | ................. | A61B 5/153 604/231 |
| 5,078,689 A * | 1/1992 | Keller | ............... | A61M 25/0606 604/174 |
| 5,338,311 A * | 8/1994 | Mahurkar | ........ | A61B 5/150526 604/110 |
| 5,879,338 A * | 3/1999 | Mahurkar | ........ | A61B 5/150389 226/129 |
| 6,217,558 B1 * | 4/2001 | Zadini | ............ | A61B 5/150244 604/164.01 |
| 6,231,564 B1 * | 5/2001 | Gambale | ........... | A61M 25/0113 604/528 |
| 6,398,743 B1 * | 6/2002 | Halseth | ............. | A61B 5/15003 604/164.12 |
| 6,547,762 B1 * | 4/2003 | Botich | ............ | A61M 25/09041 604/110 |
| 6,921,391 B1 * | 7/2005 | Barker | ............... | A61M 25/0637 604/905 |
| 7,056,306 B1 * | 6/2006 | Halseth | ............ | A61B 5/150244 604/110 |
| 8,366,685 B2 * | 2/2013 | Devgon | ........... | A61B 5/150511 604/173 |
| 9,186,100 B2 * | 11/2015 | Devgon | ................. | A61B 5/154 |
| 9,402,716 B2 * | 8/2016 | Novak | .................... | A61F 2/167 |
| 9,744,344 B1 * | 8/2017 | Devgon | ........... | A61M 39/0247 |
| 11,337,628 B2 * | 5/2022 | Burkholz | ........... | A61M 25/0113 |
| 2002/0022807 A1 * | 2/2002 | Duchon | ........... | A61M 5/14216 604/228 |
| 2004/0116853 A1 * | 6/2004 | Halseth | ................ | A61M 5/283 604/110 |
| 2004/0122373 A1 * | 6/2004 | Botich | .............. | A61M 25/0631 604/164.12 |
| 2006/0100582 A1 * | 5/2006 | Marianowicz | ..... | A61B 17/3401 604/158 |
| 2006/0200195 A1 * | 9/2006 | Yang | .................. | A61B 5/02405 604/110 |
| 2010/0106103 A1 * | 4/2010 | Ziebol | ............... | A61M 25/0105 604/265 |
| 2011/0071502 A1 * | 3/2011 | Asai | ................. | A61M 25/0606 604/528 |
| 2013/0096428 A1 * | 4/2013 | Gillies | .................. | A61M 25/01 600/434 |
| 2014/0188002 A1 * | 7/2014 | Close | ............... | A61B 5/150992 600/581 |
| 2015/0224287 A1 * | 8/2015 | Bian | ................. | A61M 25/0606 604/218 |
| 2016/0022963 A1 * | 1/2016 | Belson | ............ | A61B 5/15074 604/164.13 |
| 2017/0216564 A1 * | 8/2017 | Devgon | .......... | A61B 5/150259 |
| 2017/0360345 A1 * | 12/2017 | Devgon | .......... | A61B 5/150572 |
| 2018/0272107 A1 * | 9/2018 | Ehrenreich | ............ | A61B 5/153 |
| 2020/0016374 A1 | 1/2020 | Burkholz et al. | | |
| 2020/0129695 A1 * | 4/2020 | Brandeis | .......... | A61M 5/31581 |
| 2020/0197682 A1 * | 6/2020 | Franklin | .......... | A61M 25/0097 |
| 2021/0196903 A1 * | 7/2021 | Lampropoulos | ...... | A61M 25/01 |
| 2021/0213204 A1 * | 7/2021 | Alsuhaibani | ........ | A61M 5/3158 |
| 2021/0402153 A1 * | 12/2021 | Howell | ........... | A61M 25/09041 |

* cited by examiner

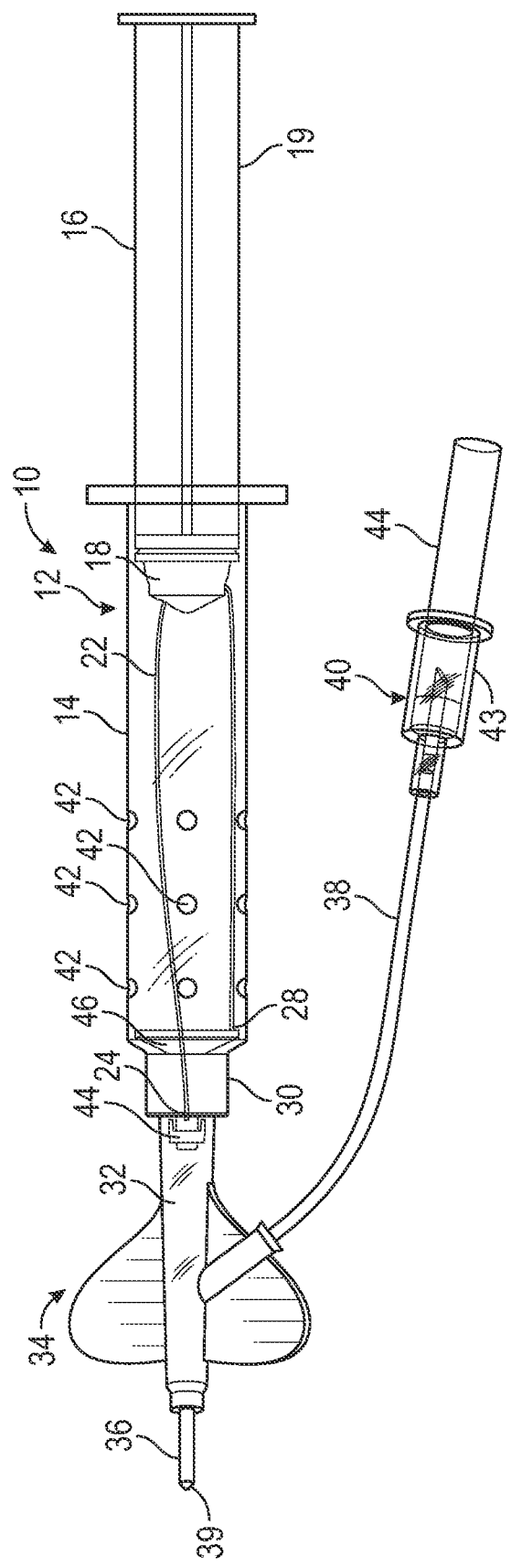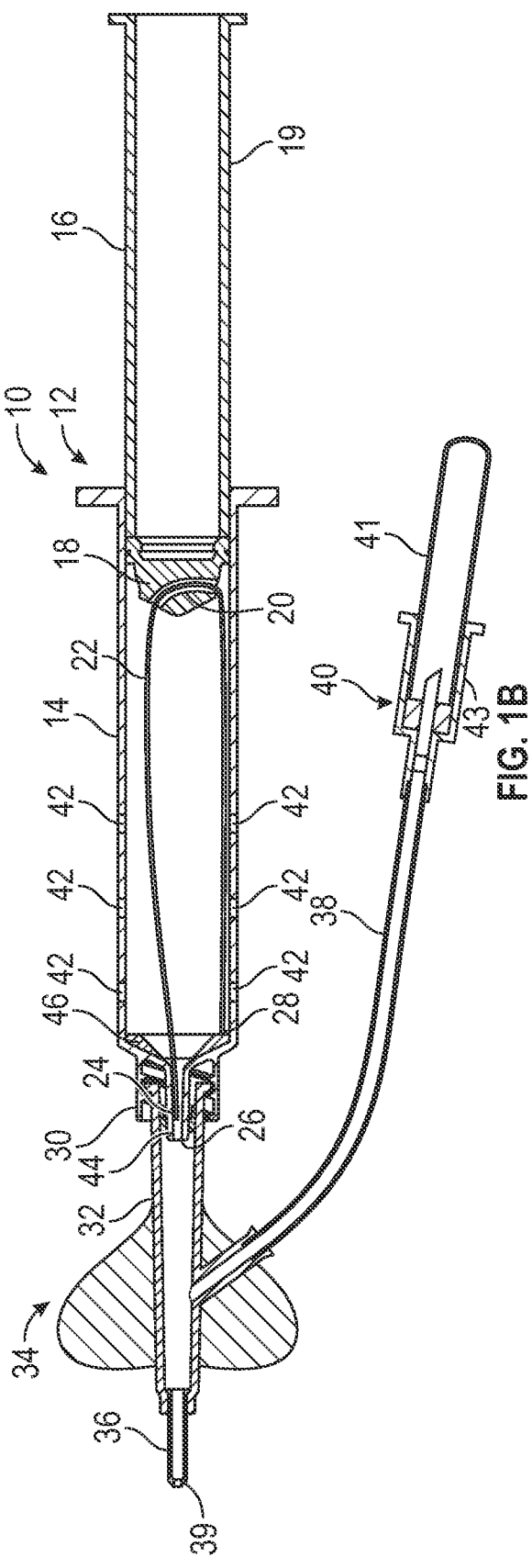

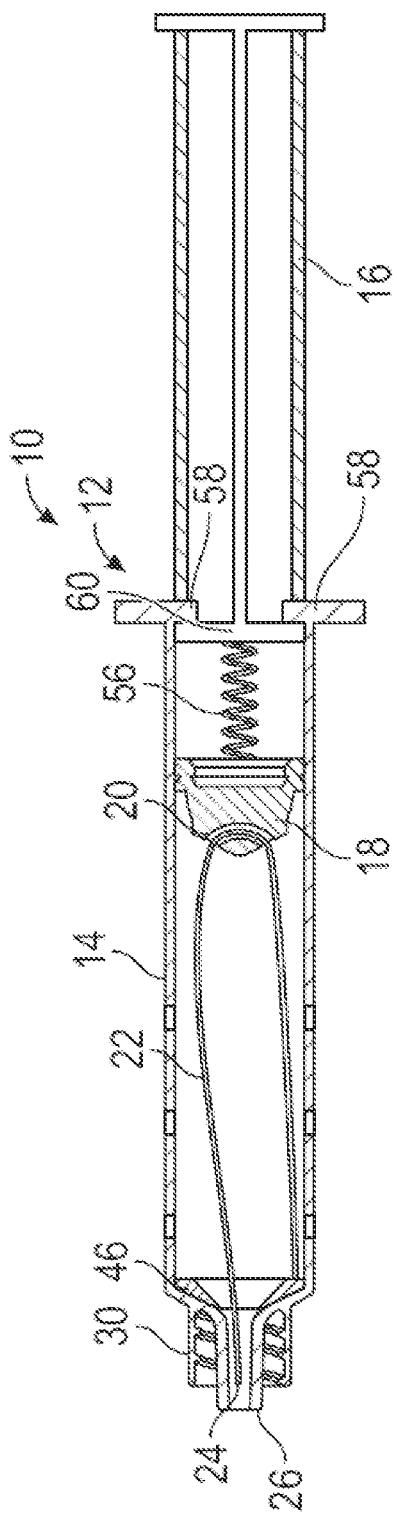
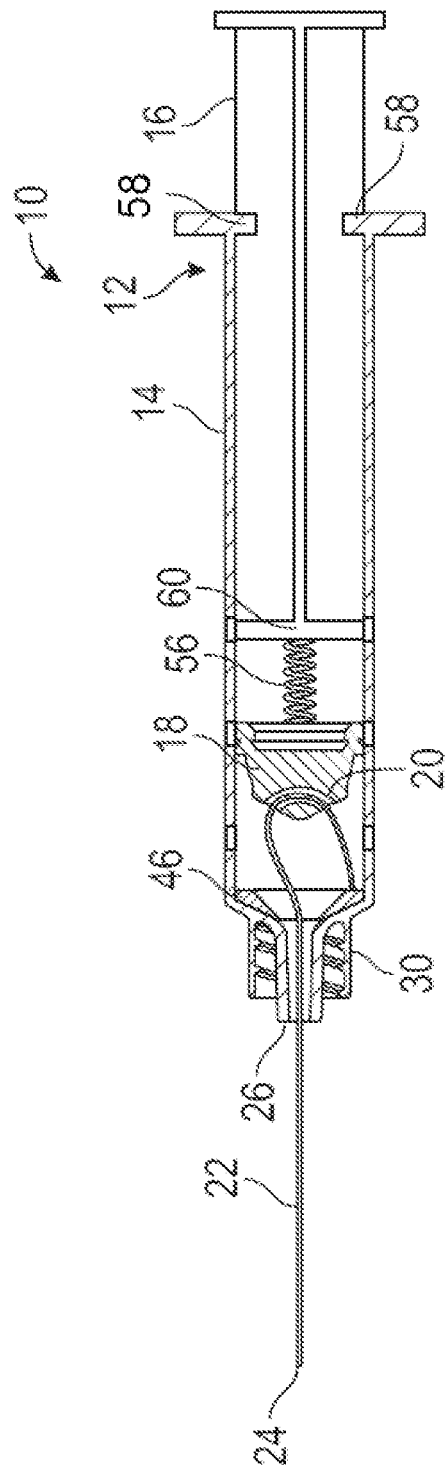
FIG. 6A
FIG. 6B

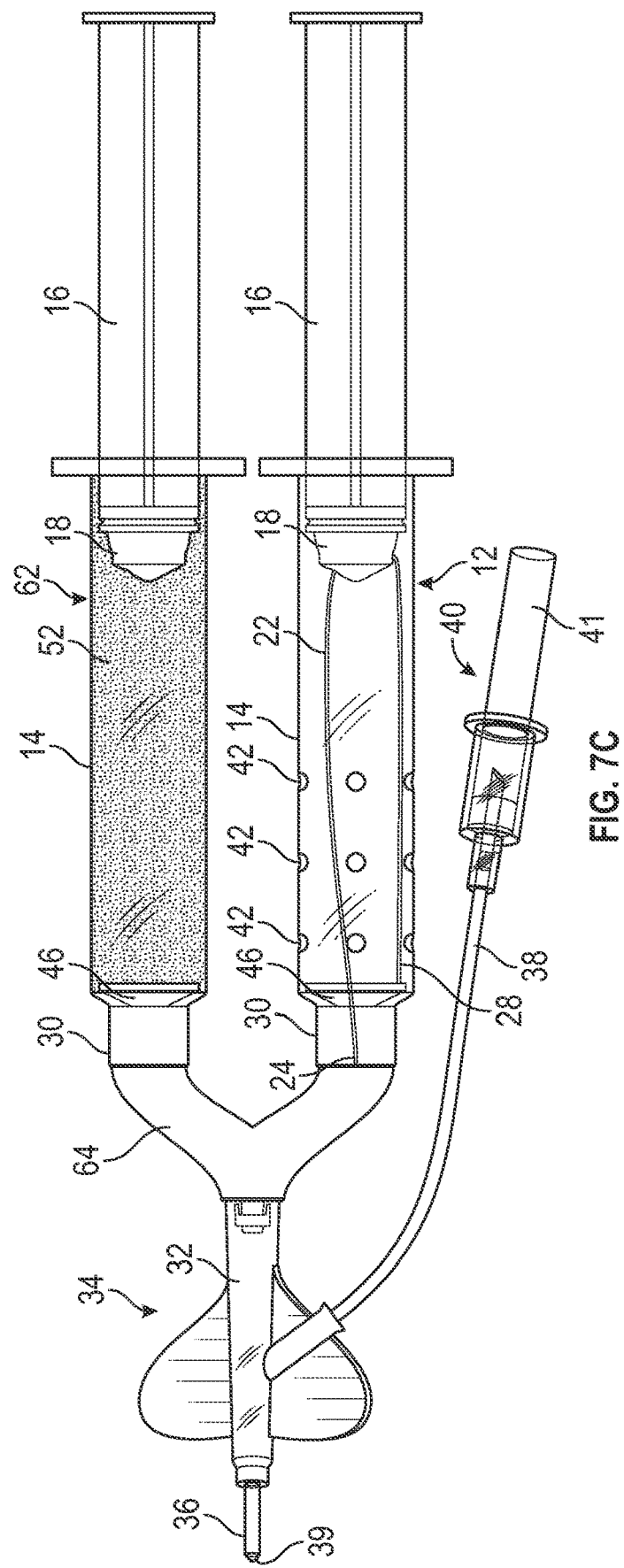

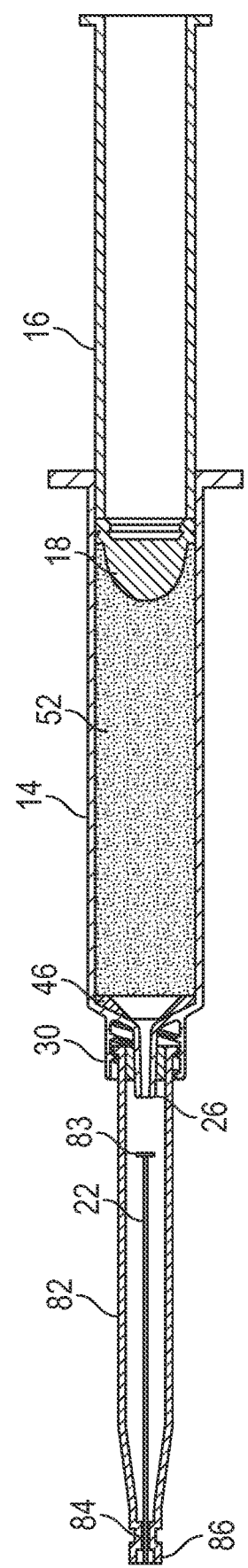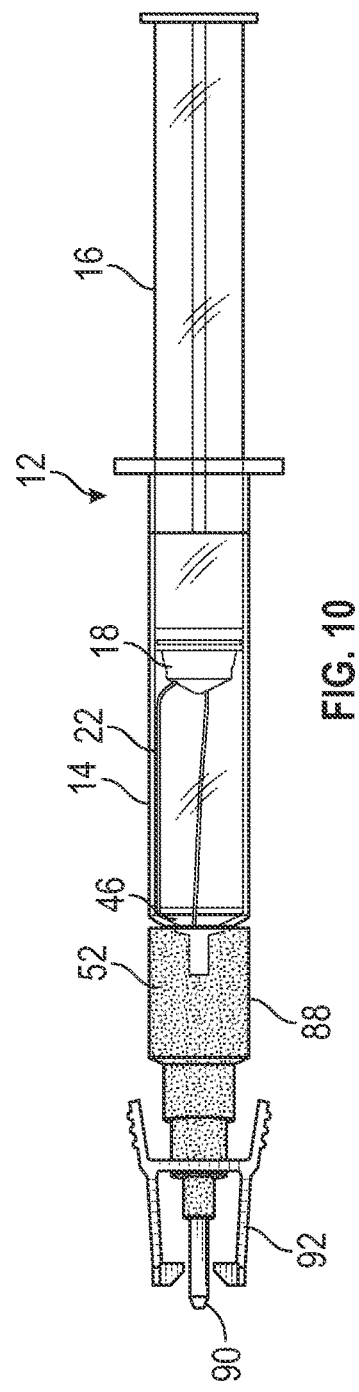
FIG. 9
FIG. 10

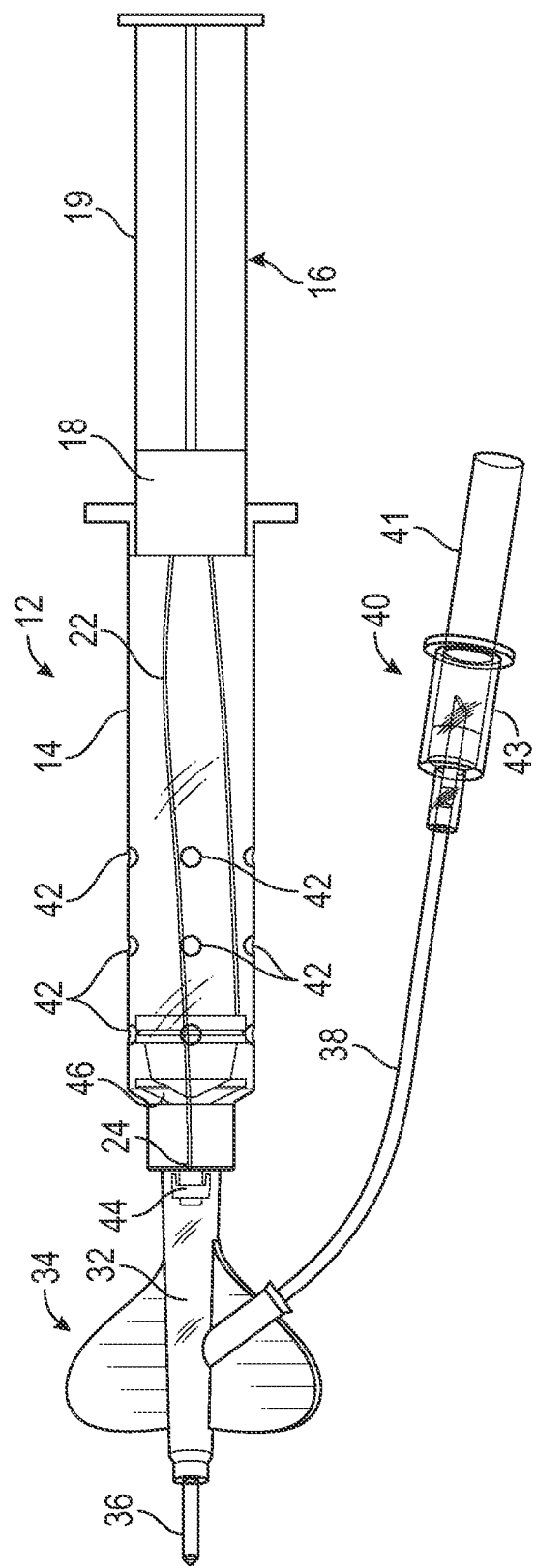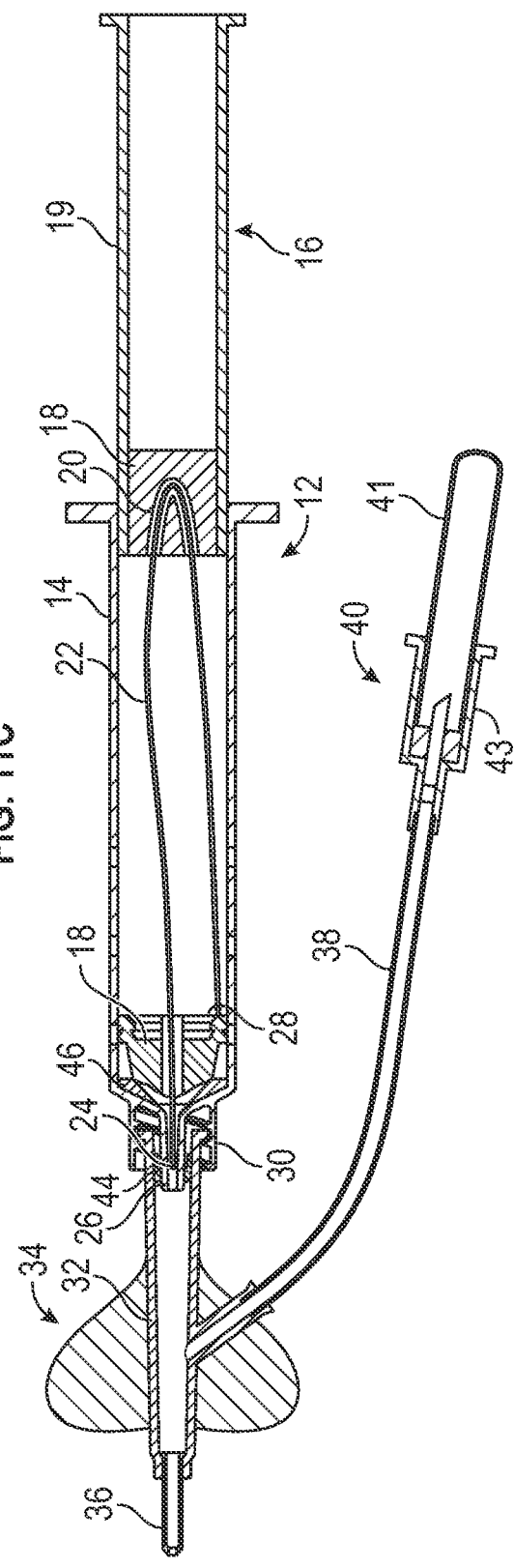

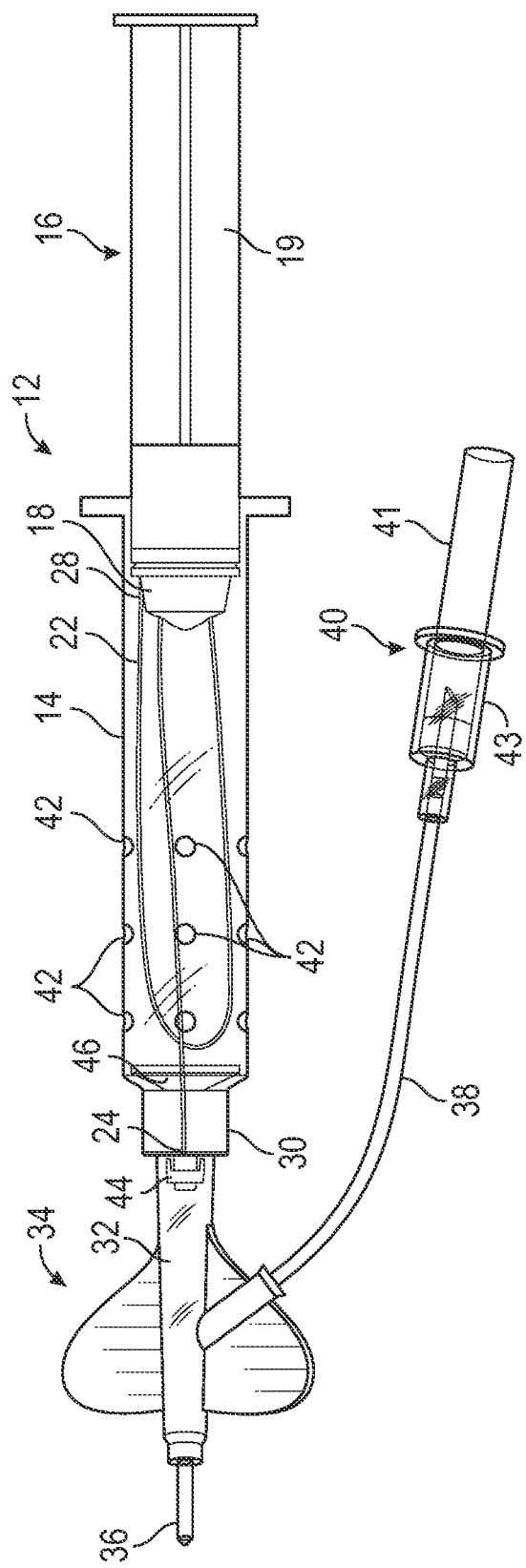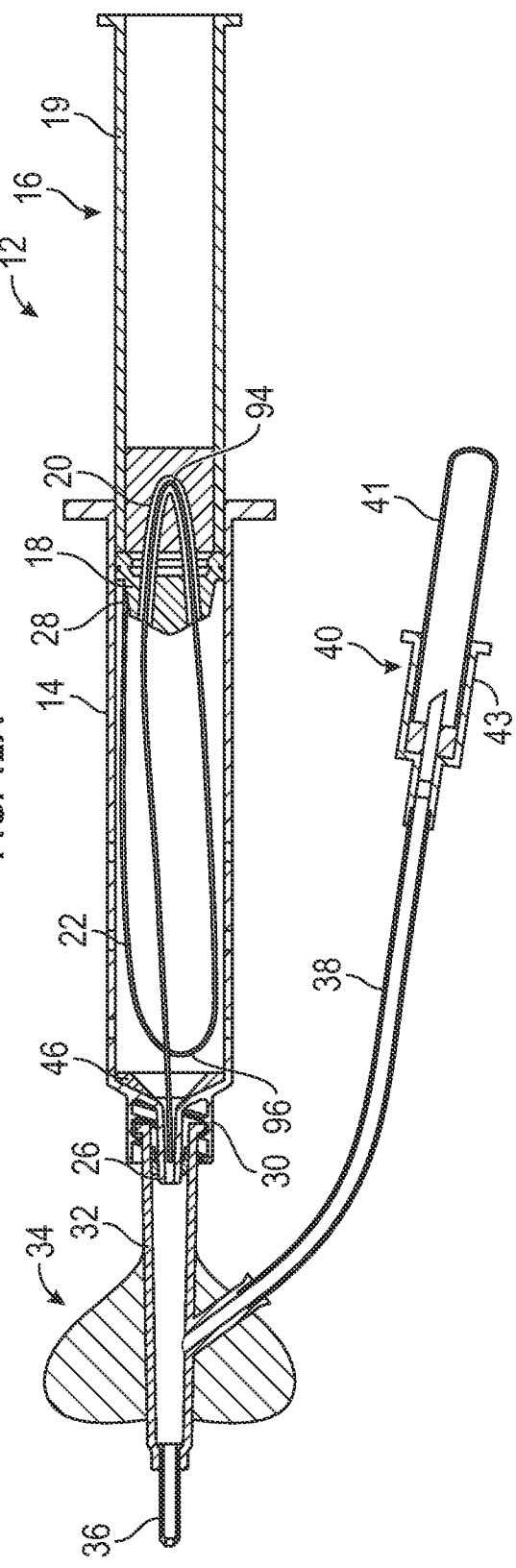
FIG. 12A
FIG. 12B ically used for a variety of infusion therapies. For example, catheters may be used for infusing fluids, such as normal saline solution, various medicaments, and total parenteral nutrition, into a patient. Catheters may also be used for withdrawing blood from the patient.

PLUNGER-BASED DELIVERY DEVICE TO FACILITATE VASCULAR ACCESS

RELATED APPLICATIONS

This application claims the benefit of U.S. Provisional Patent Application No. 62/965,641, filed Jan. 24, 2020, and entitled PLUNGER-BASED DELIVERY DEVICE TO FACILITATE VASCULAR ACCESS, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using a peripheral IV catheter may be difficult for several reasons, particularly when an indwelling time of the catheter is more than one day. For example, when the catheter is left inserted in the patient for a prolonged period of time, the catheter or vein may be more susceptible to narrowing, collapse, kinking, blockage by debris (e.g., fibrin or platelet clots), and adhering of a tip of the catheter to the vasculature. Due to this, catheters may often be used for acquiring a blood sample at a time of catheter placement but are much less frequently used for acquiring a blood sample during the catheter dwell period.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a delivery device to facilitate access to a vascular system of a patient, as well as related systems and methods. In some embodiments, the delivery device may deliver a guidewire into a catheter assembly. In some embodiments, the delivery device may include a syringe, which may include a barrel and a plunger movable within the barrel. In some embodiments, the plunger may include a handle and a stopper coupled to a distal end of the handle. In some embodiments, the stopper may include a channel, which may be U-shaped or another suitable shape.

In some embodiments, the delivery device may include a guidewire, which may be disposed within the barrel and may extend through the channel. In some embodiments, in response to depression of the plunger, the guidewire may move through the channel, and a first end of the guidewire may be advanced in the distal direction. In some embodiments, a second end of the guidewire may be fixed.

In some embodiments, the barrel may include a liquid. In some embodiments, in response to the depression of the plunger, the liquid may exit a distal opening of the syringe. In some embodiments, a diameter of the distal opening of the syringe may be greater than an outer diameter of the guidewire.

In some embodiments, air may be disposed within the barrel. In some embodiments, the barrel may include one or more vent holes. In some embodiments, in response to the depression of the plunger, the air may exit the vent holes.

In some embodiments, in response to the depression of the plunger, the stopper may be moved in the distal direction a first distance, and the first end of the guidewire may be advanced in the distal direction a second distance. In some embodiments, the second distance may be greater than the first distance. In some embodiments, the guidewire may form one or more loops.

In some embodiments, the syringe may include a flexible housing disposed within the barrel. In some embodiments, the flexible housing may prevent contact between the liquid and at least a portion of the guidewire. In some embodiments, the portion of the guidewire may be surrounded by the flexible housing. In some embodiments, the flexible housing may be configured to compress in response to the plunger being depressed in the distal direction.

In some embodiments, the syringe may include a biasing member, which may be disposed within the barrel distal to the stopper. In some embodiments, the biasing member may be compressed in response to depression of the plunger. Additionally, or alternatively, in some embodiments, another biasing member may be disposed between the stopper and the handle. In some embodiments, other biasing member may expand in response to retraction of the handle.

In some embodiments, the delivery device may include a housing, which may be coupled to the distal end of the syringe. In some embodiments, the housing may include the liquid. In some embodiments, an entirety of the guidewire may be disposed proximal to the housing.

In some embodiments, the stopper may be disposed at a distal end of the handle. In some embodiments, a U-shaped portion of the channel may be disposed within the handle. In some embodiments, another portion of the channel may extend through the stopper. In some embodiments, the other biasing member may be disposed between the U-shaped portion and the handle.

In some embodiments, in response to depression of the handle in the distal direction, the stopper may move in the distal direction to a distal position, the guidewire may move through the channel, and the first end of the guidewire may be advanced in the distal direction. In some embodiments, a second end of the guidewire may be fixed. In some embodiments, in response to retraction of the handle in the proximal direction, the stopper may remain in the distal position, the guidewire may move through the channel, and the first end of the guidewire is retracted in the proximal direction.

In some embodiments, the delivery device may include a first syringe, a guidewire, a second syringe, and an adapter. In some embodiments, the first syringe may include a first barrel and a first plunger movable within the first barrel. In some embodiments, the first plunger may include a first handle and a first stopper coupled to a distal end of the first handle. In some embodiments, the first stopper may include a channel, which may be U-shaped. In some embodiments, air may be disposed within the first barrel. In some embodiments, the first barrel may include the vent holes. In some embodiments, in response to the depression of the first plunger in the distal direction, the air may exit the vent holes.

In some embodiments, the guidewire may be disposed within the first barrel and may extend through the first channel. In some embodiments, in response to depression of the first plunger, the first guidewire may move through the channel and the first end of the guidewire may be advanced in the distal direction. In some embodiments, a second end of the guidewire may be fixed.

In some embodiments, the second syringe may include a second barrel and a second plunger movable within the second barrel. In some embodiments, the second plunger may include a second handle and a second stopper coupled to a distal end of the second handle. In some embodiments, the second barrel may contain the liquid. In some embodiments, in response to the depression of the second plunger, the liquid may exit a distal opening of the second syringe.

In some embodiments, the adapter may include a first port, a second port, and a third port. In some embodiments, the first port may be coupled to a distal end of the first syringe. In some embodiments, the second port may be coupled to a distal end of the second syringe. In some embodiments, the third port may be configured to couple to the catheter assembly.

In some embodiments, the first barrel and the second barrel may be integrally formed. In some embodiments, the first plunger may be configured to couple to the second plunger such that the first plunger and the second plunger move together. In some embodiments, the first port may be integrally formed with the first syringe and/or the second port may be integrally formed with the second port.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1A is an upper perspective of an example delivery device coupled to an example catheter assembly, illustrating an example plunger in a proximal position, according to some embodiments;

FIG. 1B is a cross-sectional view of the delivery device coupled to the catheter assembly, illustrating the plunger in the proximal position, according to some embodiments;

FIG. 6A is a cross-sectional view of the delivery device, illustrating the plunger in the proximal position and another example biasing member, according to some embodiments;

FIG. 6B is a cross-sectional view of the delivery device, illustrating the plunger in the distal position and the other biasing member, according to some embodiments;

FIG. 7C is an upper perspective view of the other delivery device, illustrating an example first plunger and an example second plunger coupled together, according to some embodiments;

FIG. 9 is a cross-sectional view of another delivery device, according to some embodiments;

FIG. 10 is an upper perspective view of another delivery device, according to some embodiments;

FIG. 11C is an upper perspective view of the delivery device coupled to the catheter assembly, illustrating another example plunger in the proximal position after being in the distal position, according to some embodiments;

FIG. 11D is a cross-sectional view of the delivery device coupled to the catheter assembly, illustrating the other plunger in the proximal position after being in the distal position, according to some embodiments;

FIG. 12A is an upper perspective view of the delivery device coupled to the catheter assembly, illustrating an example guidewire in a looped configuration, according to some embodiments;

FIG. 12B is a cross-sectional view of the delivery device coupled to the catheter assembly, illustrating the guidewire in the looped configuration, according to some embodiments;

DESCRIPTION OF EMBODIMENTS

Figure 2A:
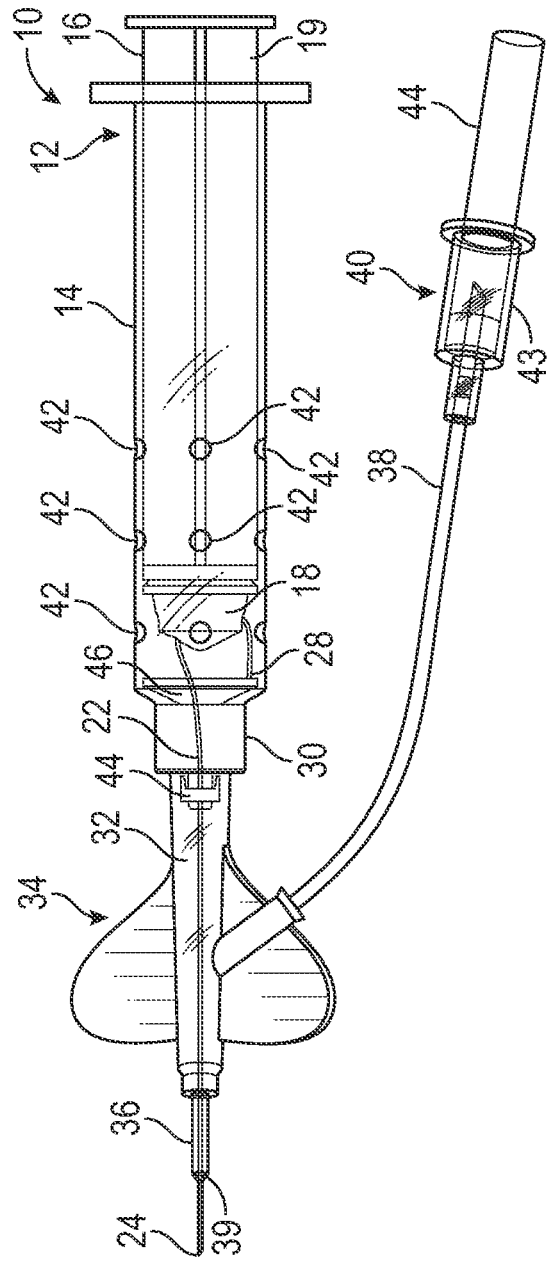
FIG. 2A is an upper perspective of the delivery device coupled to the catheter assembly, illustrating the plunger in a distal position, according to some embodiments.
Figure 2B:
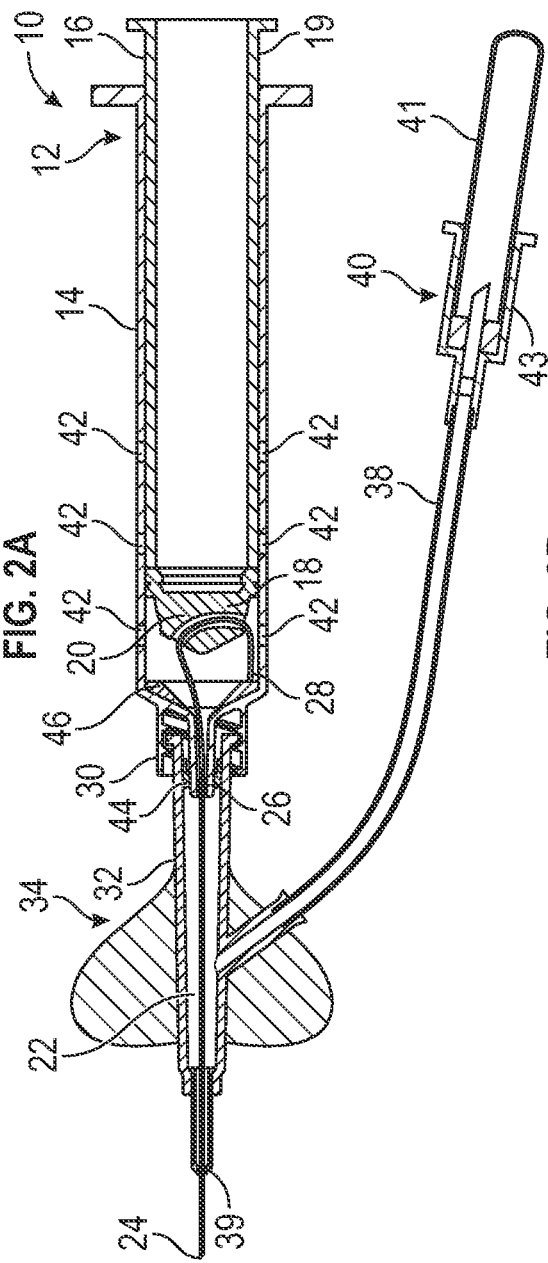
FIG. 2B is cross-sectional view of the delivery device coupled to catheter assembly, illustrating the plunger in the distal position, according to some embodiments.

Referring now to FIG. 1A-2B, in some embodiments, a delivery device 10 may include a syringe 12 having a barrel 14 and a plunger 16 movable within the barrel 14. FIGS. 1A-1B illustrate the plunger 16 of the syringe 12 in a proximal position, according to some embodiments. FIGS. 2A-2B illustrate the plunger 16 of the syringe 12 in a distal position, according to some embodiments. In some embodiments, a distal end of the plunger 16 may include a stopper 18, which may be disposed within the barrel 14. In some embodiments, the stopper 18 may be movable with a handle 19 of the plunger 16. In some embodiments, the stopper 18 may include a channel 20, which may be generally U-shaped.

In some embodiments, the delivery device 10 may include a guidewire 22, which may be disposed within the barrel 14 and may extend through the channel 20. In some embodiments, in response to movement of the plunger 16 distally, the stopper 18 may be moved distally and the guidewire 22 may be advanced distally. In some embodiments, in response to movement of the plunger 16 proximally, the stopper 18 may be moved proximally and the guidewire 22 may be retracted or withdrawn proximally.

In some embodiments, a first end 24 of the guidewire 22 may be advanced in a distal direction beyond a distal opening 26 of the syringe 12 in response to the plunger 16 being partially and/or fully depressed within the barrel 14 in the distal direction, as illustrated, for example, in FIGS. 2A-2B. In some embodiments, a second end 28 of the guidewire 22 may be secured or fixed within the delivery device 10. In some embodiments, the second end 28 of the guidewire 22 may be fixed within the barrel 14 or a distal connector 30 of the syringe 12. In some embodiments, the first end 24 of the guidewire 22 may be blunt and/or tapered, which may decrease a likelihood of trauma to vasculature of a patient in case of contact with the guidewire 22. In some embodiments, the guidewire 22 may include metal or another suitable material.

In some embodiments, a catheter adapter 32 of a catheter assembly 34 may be coupled to the syringe 12. In further detail, in some embodiments, a distal end 26 of the syringe 12 may include the distal connector 30, which may be configured to couple to a proximal end of the catheter adapter 32. In some embodiments, the distal connector 30 may include a luer adapter, such as a slip or thread male or slip or thread female luer adapter, or another suitable connector.

In some embodiments, a needleless connector (not illustrated) may connect the syringe 12 to the catheter adapter 32. In further detail, in some embodiments, the distal connector 30 may be configured to couple to a proximal end of the needleless connector, which may be coupled to the proximal end of the catheter adapter 32. In some embodiments, the needleless connector may include a pro re nata ("PRN") connector. In some embodiments, the needleless connector may include a SMARTSITE™ Needle-Free Connector available from Becton, Dickinson and Company of Franklin Lakes, New Jersey, a Q-SYTE™ Luer Activated Split Septum available from Becton, Dickinson and Company of Franklin Lakes, New Jersey, an INTERLINK™ Needlefree System available from Baxter International Inc., or another other suitable needleless connector.

In some embodiments, the catheter assembly 34 may include a catheter 36, which may be secured within the catheter adapter 32 and may extend distally from the catheter adapter 32. In some embodiments, the catheter 36 may include a peripheral intravenous catheter, a peripherally-inserted central catheter, or a midline catheter. In some embodiments, the catheter 36 may be dwelling within vasculature of the patient when the delivery device 10 is coupled to the catheter assembly 34. In some embodiments, the catheter adapter 32 may be integrated, having an integrated extension tube 38, or non-integrated, without the integrated extension tube 38.

In some embodiments, a blood collection device 40 may be coupled to the extension tube 38. In some embodiments, the blood collection device 40 may include a vacuum tube, a test tube 41, a syringe, or another suitable blood collection container. In some embodiments, the blood collection device 40 may include a holder 43, which may be configured to hold the test tube 41, as illustrated, for example, in FIGS. 1A-2B. In some embodiments, the blood collection device 40 may include the VACUTAINER® one-use holder, available from Becton, Dickinson and Company of Franklin Lakes, New Jersey.

In some embodiments, the delivery device 10 may allow the guidewire 22 to access the vasculature of the patient through the catheter 36, which may be inserted into the vasculature of the patient. In some embodiments, the syringe 12 may be used to advance the guidewire 22 beyond a distal tip 39 of the catheter 36 to overcome obstructions such as thrombus, valves, and/or a fibrin sheath in or around the distal tip 39 of the catheter 36 that may otherwise prevent blood collection within the blood collection device 40. Thus, in some embodiments, the delivery device 10 may extend a life or dwell period of the catheter 36 within the vasculature.

In some embodiments, the catheter assembly 34 may include a needle hub coupled to the proximal end of the catheter adapter 32 and an introducer needle extending distally from the needle hub (not illustrated). In some embodiments, the needle hub and the introducer needle may be removed from the catheter assembly 34 in response to placement of the catheter 36 within vasculature of the patient, and the delivery device 10 may be coupled to the proximal end of the catheter adapter 32 after the needle hub and the introducer needle are removed.

In some embodiments, the stopper 18 and the channel 20 may be oriented in various ways and angles within the barrel 14. For example, the channel 20 may be generally horizontally or vertically oriented within the barrel 14 when the delivery device 10 is coupled with the catheter adapter 32 positioned for insertion into a patient. In some embodiments, the barrel 14 and/or the plunger 16 may be cylindrical, square, or another shape.

In some embodiments, the barrel 14 may include a liquid, such as, for example, saline or another suitable flushing liquid. In some embodiments, the liquid may flush the catheter assembly 34 in response to depression of the plunger 16. In some embodiments, in response to depression of the plunger 16, the liquid may exit the distal opening 26 of the syringe 12. In some embodiments, a diameter of the distal opening 26 of the syringe 12 may be greater than an outer diameter of the guidewire 22, such that the guidewire 22 may exit the distal opening 26 and/or the liquid may flow around the guidewire 22. In some embodiments, in response to depression of the plunger 16, the liquid may flow around the guidewire 22 and into and/or through the catheter assembly 34.

In some embodiments, the barrel 14 may not include the liquid. In some embodiments, the barrel 14 of the syringe 12 may include one or more vent holes 42, which may allow air to escape the barrel 14 in response to depression of the plunger 16 or movement of the plunger in the distal direction. In some embodiments, the vent holes 42 may prevent air from entering the catheter assembly 34.

In some embodiments, the channel 20 may contact and support the guidewire 22. In some embodiments, the plunger 16 may be depressed or moved in the distal direction from the proximal position. In some embodiments, in response to depression of the plunger 16, the stopper 18 may be moved in the distal direction a first distance, the guidewire 22 may move through the channel 20, and the first end 24 of the guidewire 22 may be advanced in the distal direction a second distance, which may be greater than the first distance. In some embodiments, the second distance may be two times the first distance ("a 1:2 advancement ratio") due to the U-shape of the channel 20. In some embodiments, the second distance may be at least two times the first distance. In some embodiments, the delivery device 10 and the 1:2 advancement ratio (or another advancement ratio where the second distance is greater than the first distance) between the stopper 18 and the first end 24 of the guidewire 22 may provide reliability and structural support as the guidewire 22 is distally advanced, while also providing a guidewire 22 with long reach.

In some embodiments, a septum 44 may be disposed within the catheter adapter 32 and may be penetrated in response to coupling of the delivery device 10 to the catheter adapter 32. In some embodiments, a distal end of the barrel 14 may include a secondary stopper 46, which may include rubber or another suitable material. In some embodiments, the secondary stopper 46 may prevent the liquid from flowing out the distal end of the barrel 14 or through the secondary stopper 46. In some embodiments, in response to depression of the plunger 16 in the distal direction, the secondary stopper 46 may be configured to allow liquid to flow through the secondary stopper 46. In some embodiments, the secondary stopper 46 may contact the stopper 18 in response to the plunger 16 being moved to the distal position. In some embodiments, the distal position may correspond to a fully depressed position. In some embodiments, the secondary stopper 46 may be spaced apart from the stopper 18 in response to the plunger 16 being moved to the distal position. In some embodiments, the second end 28 may contact and/or be coupled to the secondary stopper 46.

Figure 3A:
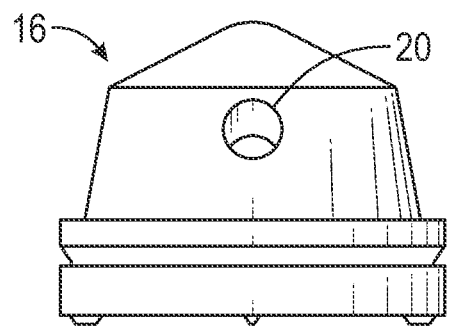
FIG. 3A is a side view of an example stopper, according to some embodiments.
Figure 3B:
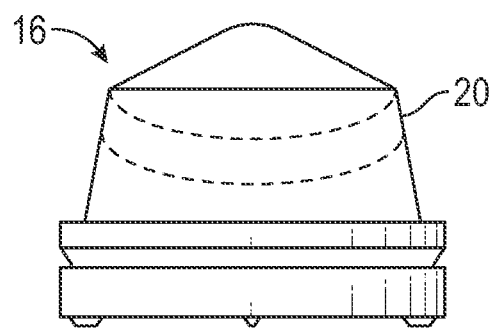
FIG. 3B is another side view of the stopper, according to some embodiments.
Figure 3C:
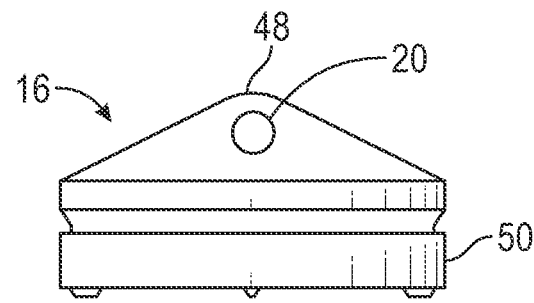
FIG. 3C is a side view of another stopper, according to some embodiments.
Figure 3D:
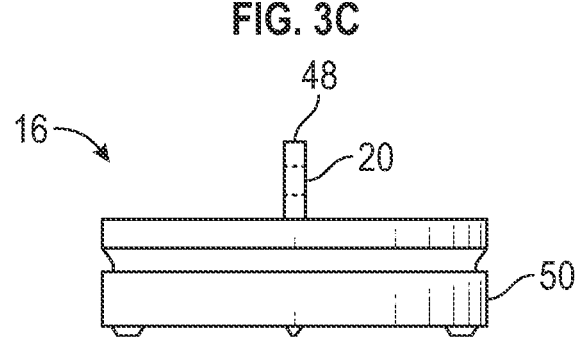
FIG. 3D is another side view of another stopper, according to some embodiments.

Referring now to FIGS. 3A-3B, in some embodiments, the channel 20 may extend through the plunger 16, from one side to another. Referring now to FIGS. 3C-3D, in some embodiments, a distal end 48 of the plunger 16 may include a smaller outer diameter than a proximal portion 50 of the plunger 16 that may contact an inside of the barrel 14. In some embodiments, the channel 20 may extend through the distal end 48 of the plunger 16, which may shorten the channel 20 and provide less contact and friction between the channel 20 and the guidewire 22. In some embodiments, the distal end 48 may include two opposing stepped surfaces, which may cutaway a portion of the distal end 48 to facilitate the channel 20 being shorter.

Figure 4:
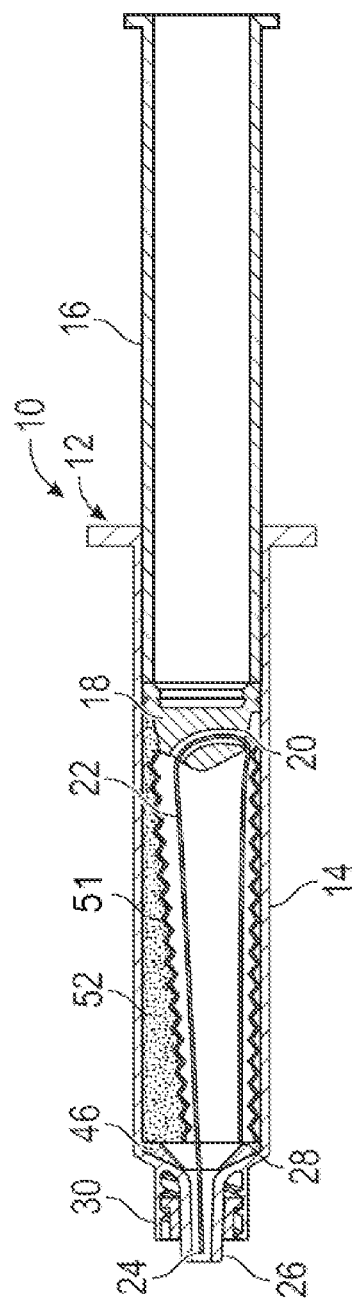
FIG. 4 is a cross-sectional view of the delivery device, illustrating an example flexible housing, according to some embodiments.

Referring now to FIG. 4, in some embodiments, at least a portion of the guidewire 22 may be disposed in a housing 51, which may be flexible. In some embodiments, the housing 51 may be accordion-like and/or compressible in response to depression of the plunger 16. In some embodiments, the housing 51 may include flexible plastic. In some embodiments, a proximal end of the housing 51 may be coupled to the plunger 16. In some embodiments, the housing 51 may surround a portion of the guidewire 22 between the first end 24 and the second end 28. In some embodiments, the housing 51 may surround the first end 24 and/or the second end 28. In some embodiments, the housing 51 may prevent contact of at least a portion of the guidewire 22 with the liquid 52, which may be disposed within the barrel 14. In some embodiments, in response to depression of the plunger 16 or movement of the plunger 16 from the proximal position to the distal position, the first end 24 may puncture and/or exit a distal end of the housing 51.

Figure 5A:
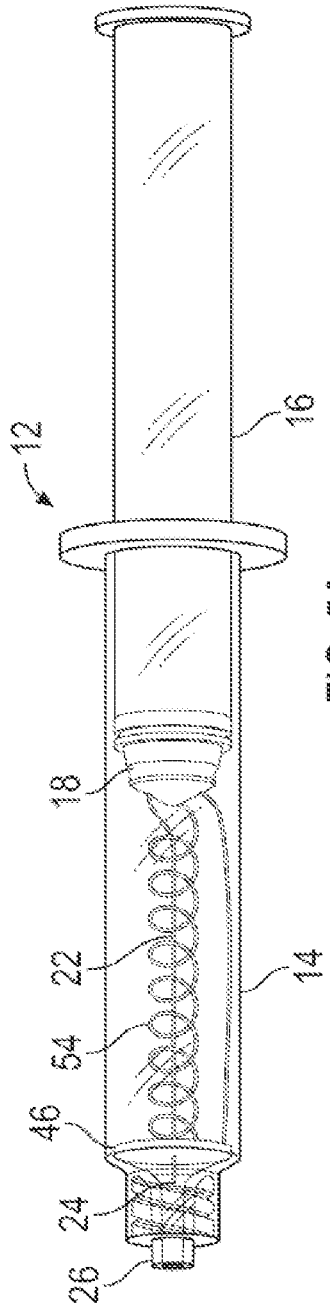
FIG. 5A is an upper perspective view of the delivery device, illustrating the plunger in the proximal position and an example biasing member, according to some embodiments.
Figure 5B:
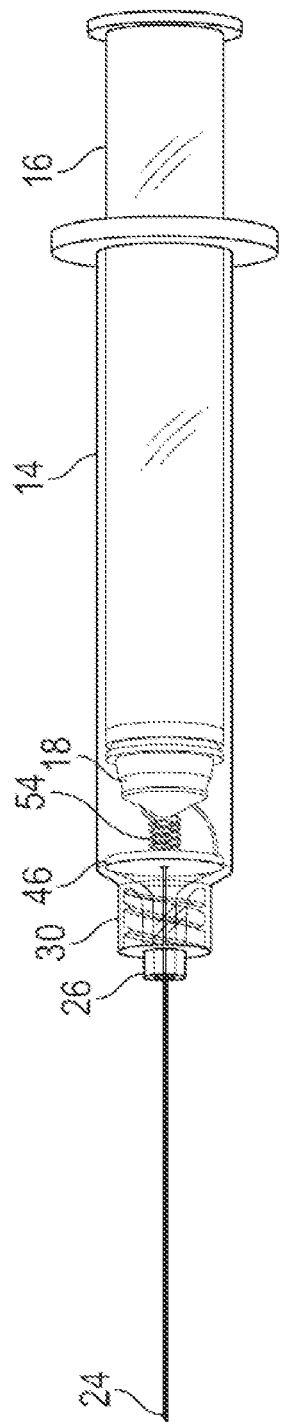
FIG. 5B is an upper perspective view of the delivery device, illustrating the plunger in the distal position and the biasing member, according to some embodiments.

Referring now to FIGS. 5A-5B, in some embodiments, a biasing member 54 may be disposed within the barrel 14 distal to the stopper 18. In some embodiments, a proximal end of the biasing member 54 may be coupled to the plunger 16. In some embodiments, a distal end of the biasing member 54 may be coupled to the secondary stopper 46, the inner surface of the barrel 14, or another suitable location. In some embodiments, the biasing member 54 may include a coil spring, which may include a variable or uniform pitch. In some embodiments, the coil spring may include a compression spring. In some embodiments, the coil spring may include a smaller pitch near the distal tip 39 of the catheter 36 (see, for example, FIGS. 1A-2B), which may prevent blood clots from entering the syringe 12 but still allow blood to flow into the syringe 12.

In some embodiments, the biasing member 54 may include metal, an elastomer, or another suitable material. In some embodiments, the biasing member 54 may reduce a force at which the clinician depresses the plunger 16, which may reduce a likelihood of hemolysis.

Referring now to FIGS. 6A-6B, in some embodiments, a biasing member 56 may be disposed within the barrel 14 proximal to the stopper 18. In some embodiments, a distal end of the biasing member 56 may be coupled to the stopper 18 or another suitable location. In some embodiments, a proximal end of the biasing member 56 may be coupled to plunger 16 or another suitable location. In some embodiments, such as in, for example, FIGS. 11A-12B, the biasing member 56 may be disposed between a U-shaped portion of the channel 20 and a distal end of the handle 19.

In some embodiments, the biasing member 56 may include a coil spring, which may include a variable or uniform pitch. In some embodiments, the coil spring may include a tension spring. In some embodiments, the coil spring may include a smaller pitch near the distal opening 26 of the syringe 12, which may prevent blood clots from entering the syringe 12 but still allow blood to flow into the syringe 12.

In some embodiments, the biasing member 56 may include metal, an elastomer, or another suitable material. In some embodiments, the biasing member 56 may reduce a force at which the clinician retracts the plunger 16 or moves the plunger in the proximal direction, which may reduce a likelihood of hemolysis. In some embodiments, the inner surface of the barrel 14 may include one or more protrusions 58, which may be configured to contact a portion of the plunger 16, such as, for example, a base 60, to prevent the plunger from being proximally removed from the barrel 14.

Figure 7A:
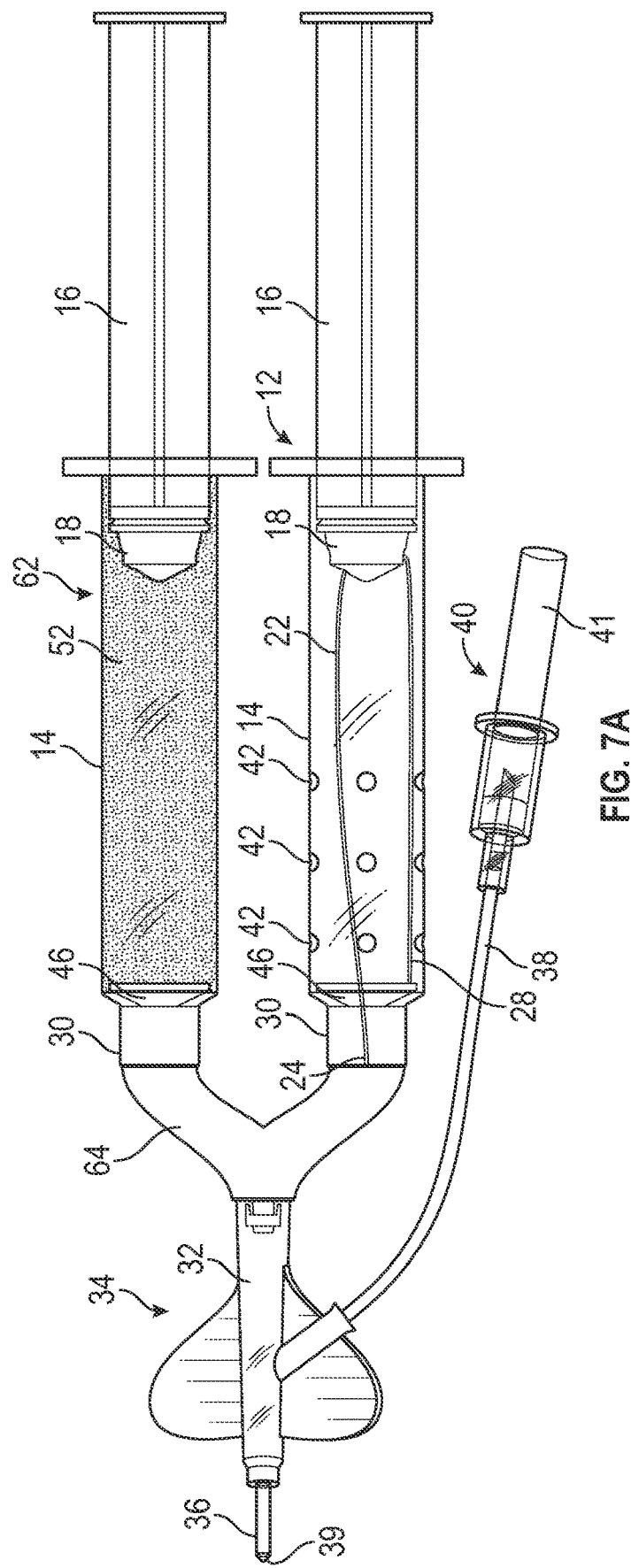
FIG. 7A is an upper perspective view of another delivery device, according to some embodiments.

Referring now to FIG. 7A, in some embodiments, a catheter system may include the syringe 16 and a syringe 62, which may both be coupled to a Y-shaped adapter 64. In some embodiments, the Y-shaped adapter 64 may be coupled to catheter adapter 32. In some embodiments, the Y-shaped adapter 64 may include three or more ports, one or more of which may include a luer adapter or another suitable connector.

In some embodiments, the syringe 62 may be similar or identical to the syringe 12 of FIGS. 1-6 in terms of one or more features and/or operation. In some embodiments, the barrel 14 of the syringe 62 may be filled with the liquid 52, which may flow distally through the adapter 32 and the catheter assembly 34 in response to depression of a plunger 16 of the syringe 62. In some embodiments, the syringe 62 may be used to flush the catheter assembly 34 before and/or during distal advancement of the guidewire 22 using the syringe 12. In some embodiments, the syringe 62 may be used to flush the catheter assembly 34 following blood draw.

In some embodiments, the Y-shaped adapter 64 may be integrally formed with the syringe 12 and/or the syringe 62. Additionally, or alternatively, in some embodiments, the Y-shaped adapter 64 may be integrally formed with the catheter adapter 32. In some embodiments, the plungers 16 of the syringe 12 and the syringe 62 may move independently of each other, allowing the clinician to control an amount of the liquid 52 that is flushed into the vasculature separately from insertion of the guidewire 22 into the vasculature. In some embodiments, the Y-shaped adapter 64 may be monolithically formed with the syringe 12 and/or the syringe 62 as a single unit.

Figure 7B:
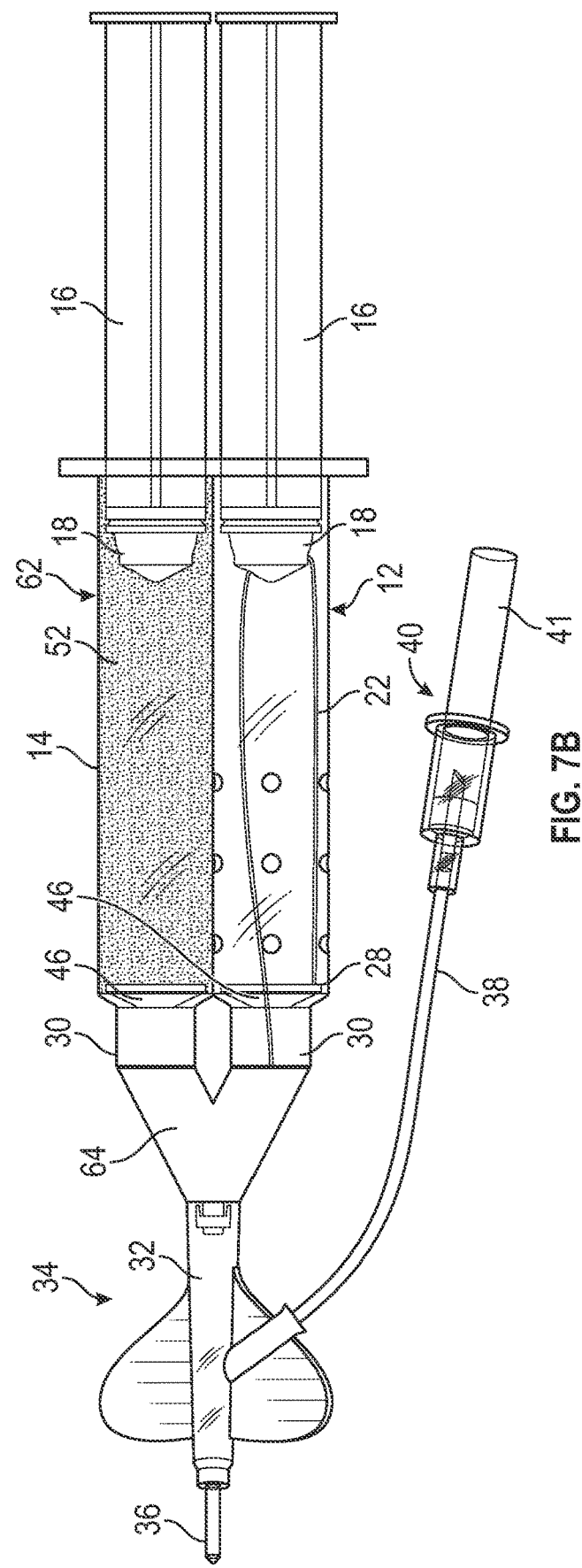
FIG. 7B is an upper perspective view of the other delivery device, illustrating an example first syringe and an example second syringe coupled together, according to some embodiments.

Referring now to FIG. 7B, in some embodiments, the barrels 14 of the syringe 12 and the syringe 62 may be integrally formed, which may ease handling by the clinician. In some embodiments, the plungers 16 of the syringe 12 and the syringe 62 may move independently of each other. In other embodiments, the plungers 16 of the syringe 12 and the syringe 62 may be coupled together such that they move together, which may facilitate ease of handling and operation for the clinician. Referring now to FIG. 7C, the plungers 16 of the syringe 12 and the syringe 62 may be coupled together, according to some embodiments.

Figure 8:
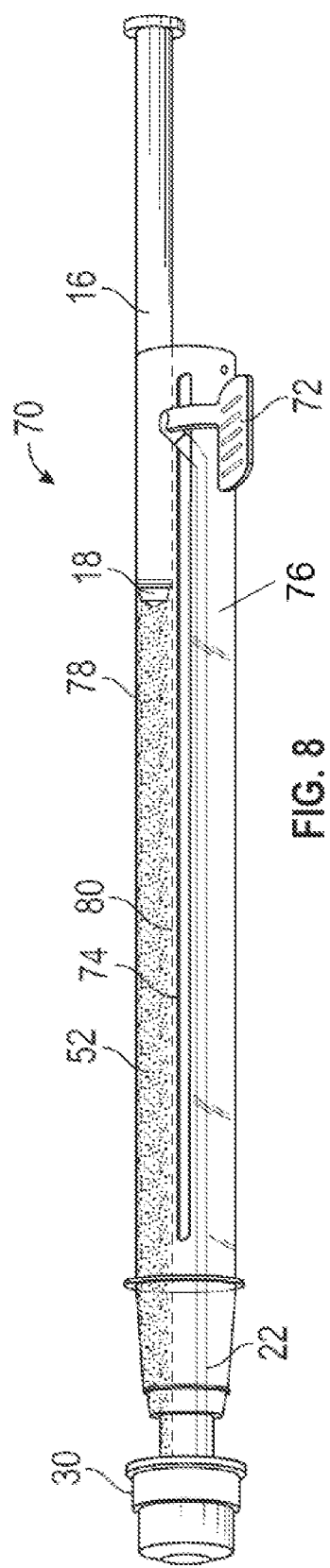
FIG. 8 is an upper perspective view of another delivery device, illustrating an example plunger and an example advancement element in a proximal position, according to some embodiments.
Figure 11A:
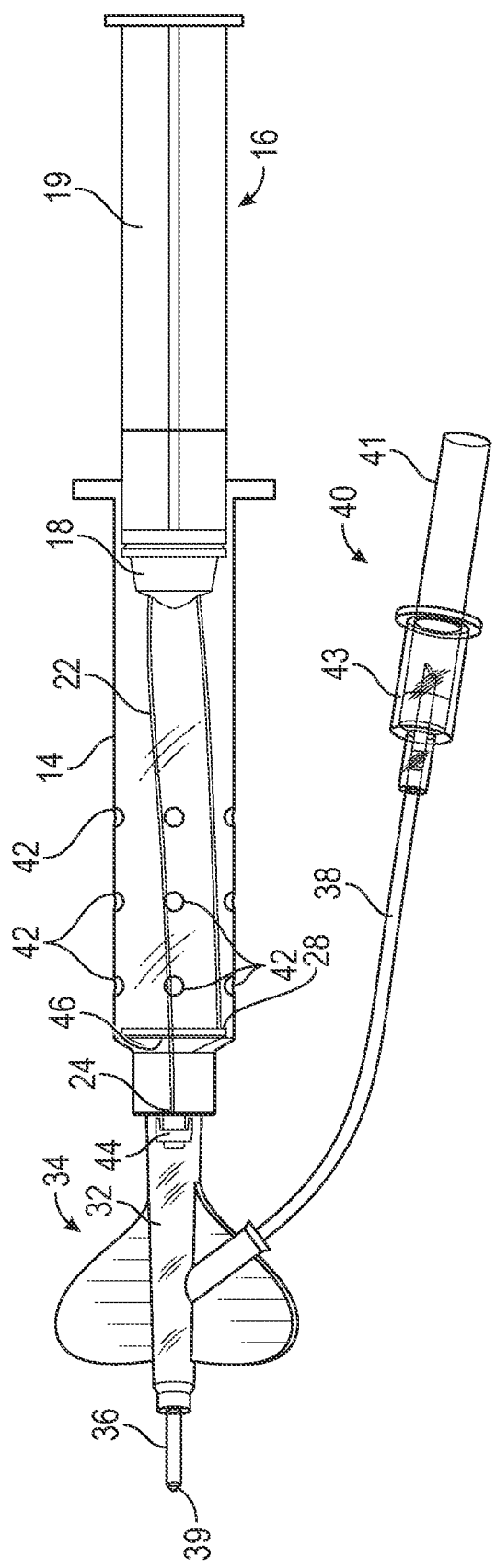
FIG. 11A is an upper perspective view of the delivery device coupled to the catheter assembly, according to some embodiments.
Figure 11B:
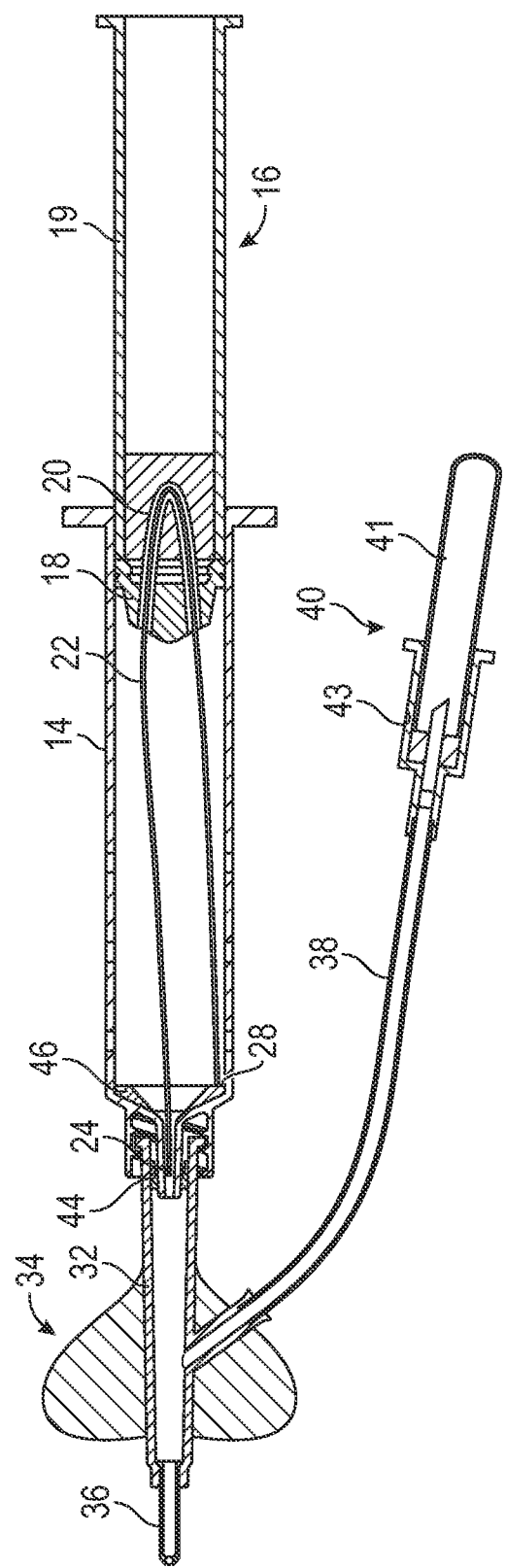
FIG. 11B is a cross-sectional view of the delivery device coupled to the catheter assembly, according to some embodiments.

In some embodiments, the syringe 12 (see FIGS. 7A-7C) may be replaced with another delivery device that includes another guidewire advancement mechanism, such as, for example, a rotary advancement element or a linear advancement element. Referring now to FIG. 8, in some embodiments, a delivery device 70 may include an advancement element 72. In some embodiments, the advancement element 72 may include a tab or a grip, which may be moved by the clinician to advance the guidewire 22 in the distal direction and/or retract the guidewire 22 in a proximal direction. In some embodiments, the advancement element 72 may be coupled to a proximal end of the guidewire 22. In some embodiments, the advancement element may be slidable along a slot 74 disposed within a housing 76, as illustrated in FIG. 8.

In some embodiments, the housing 76 may include a syringe-portion 78, which may be identical or similar to the syringe 62 discussed with respect to FIGS. 7A-7C in terms of one or more features and/or operation. In some embodiments, a wall 80 may separate the syringe-portion 78 from a portion of the housing 76 that includes guidewire 22. Thus, in some embodiments, the liquid within the syringe-portion 78 may be separated within the delivery device 70 from the portion of the housing 76 that includes the guidewire 22. In some embodiments, the advancement element 72 and a plunger 16 of the syringe-portion 78 may be advanced and/or retracted independently of each other. In some embodiments, a distal end of the housing 76 may include the distal connector 30. In some embodiments, the syringe 62 (see, for example, FIGS. 7A-7B) may be coupled to a proximal end of the housing 76, which may not include the syringe-portion.

Figure 7D:
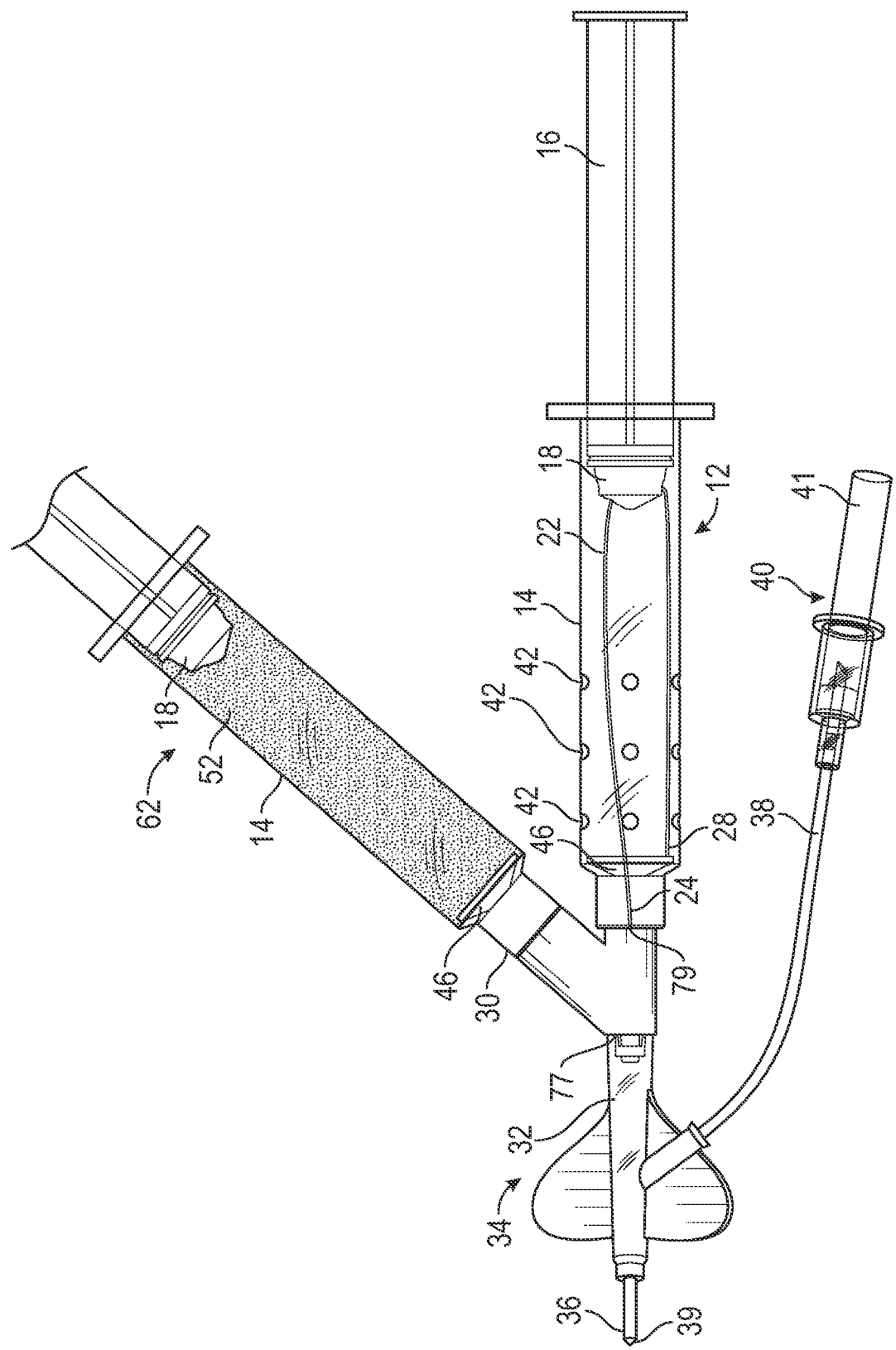
FIG. 7D is an upper perspective view of the other delivery device, according to some embodiments.

Referring now to FIG. 7D, in some embodiments, a path of the guidewire 22 as the guidewire 22 moves in the distal direction may be generally straight. In some embodiments, a distal port 77 and a proximal port 79 of the adapter 32 may be generally aligned with the syringe 12 such that the path of the guidewire 22 as the guidewire 22 moves in the distal direction is generally straight. In some embodiments, movement of the guidewire in the distal direction according to a generally straight path may be accomplished in various ways, such as, for example, different size barrels 14 between the syringe 12 and the syringe 62.

Referring now to FIG. 9, in some embodiments, the syringe 62 may be coupled to a housing 82, which may include the guidewire 22. In some embodiments, in response to depression of the plunger 16, the liquid 52 may flow distally through the housing 82 and flush the guidewire 22 into the catheter adapter and beyond a distal tip of a catheter extending from a catheter adapter. In some embodiments, a proximal end of the guidewire 22 may include an enlarged diameter portion 83, which may catch on a portion of the housing 82, such as a distal opening 84, or a portion of the catheter adapter to prevent additional distal movement of the guidewire 22. In some embodiments, a distal end of the housing 82 may include a distal connector 86, which may be coupled to the catheter adapter. In some embodiments, the distal connector 86 may include a slip or thread male or slip or thread female luer adapter, or another suitable connector.

Referring now to FIG. 10, in some embodiments, the distal connector 30 of the syringe 12 may be coupled to a housing 88, which may be filled with the liquid 52. In some embodiments, in response to depression of the plunger 16, the liquid 52 may flow distally through a distal opening 90 of the housing 82 and flush a catheter assembly, which may be coupled to a distal connector 92 of the housing 82. In some embodiments, the distal connector 92 may include a slip or thread male or slip or thread female luer adapter, or another suitable connector. In some embodiments, the housing 82 may prevent contact between the liquid 52 and the guidewire 22 before the plunger 16 is depressed. In some embodiments, in response to depression of the plunger 16, the guidewire 22 may be advanced distally through the housing 88 and through the catheter assembly.

Referring now to FIGS. 11A-11D, in some embodiments, the stopper 18 may not be coupled to the handle 19 of the plunger 16. In some embodiments, in response to the handle 19 being in a proximal position, as illustrated, for example, in FIGS. 11A-11B, the stopper 18 may be proximate a distal end of the handle 19. In some embodiments, in response to the handle 19 being moved from the proximal position to a distal position, the stopper 18 may be moved distally. In some embodiments, in response to retracting the handle 19 in the proximal direction after moving the handle 19 from the proximal position to the distal position, the stopper 18 may remain, as illustrated, for example, in FIGS. 11C-11D. In these embodiments, the channel 20 may be disposed within a distal portion of the handle 19 and the stopper 18. In some embodiments, after completing blood collection, the handle 19 may be retracted in the proximal direction, but the stopper 18 may remain and prevent blood from entering the syringe 12.

Referring now to FIGS. 12A-12B, in some embodiments, the plunger 16 may be depressed or moved in the distal direction from the proximal position. In some embodiments, in response to depression of the plunger 16 in the distal direction a first distance, the guidewire 22 may move through the channel 20 and the first end 24 of the guidewire 22 may be advanced in the distal direction a second distance, which may be greater than the first distance. In some embodiments, the guidewire 22 may form one or more loops when the plunger 16 is in the proximal position. In these embodiments, the guidewire 22 may include multiple bends or U-shaped portions. In some embodiments, the guidewire 22 may include a first U-shaped portion 94 and a second U-shaped portion 96, as illustrated, for example, in FIGS. 12A-12B. In some embodiments, the second end 28 may be coupled to the plunger 16, the inner surface of the barrel 14, or another suitable location. In some embodiments, the second distance may be more than two times the first distance due to the multiple bends and looped configuration of the guidewire 22.

Figure 13A:
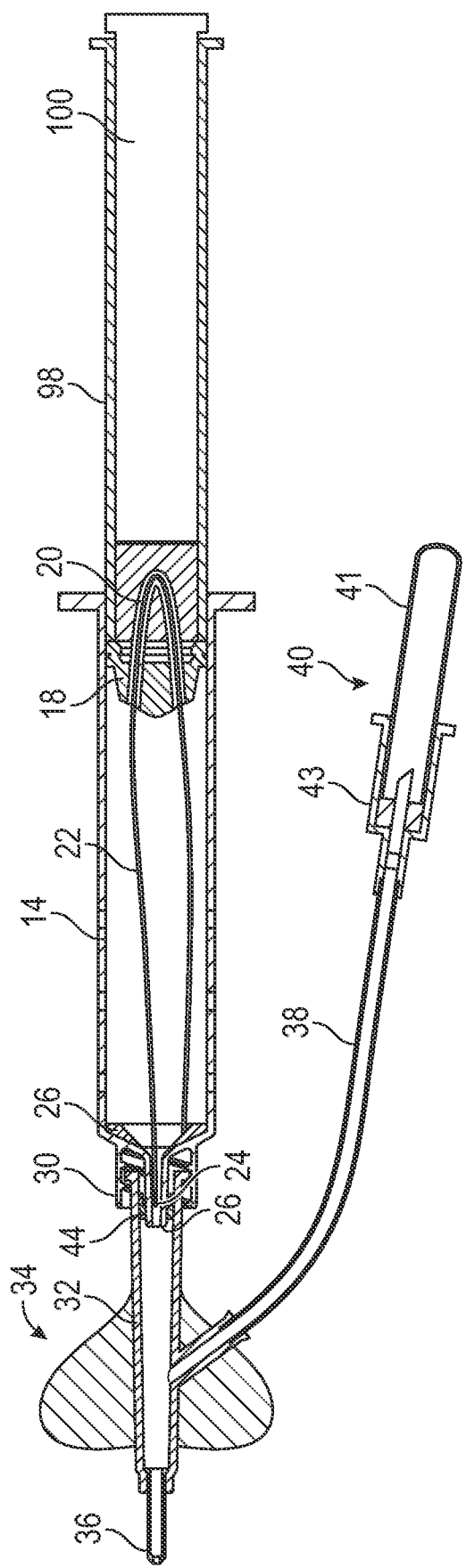
FIG. 13A is a cross-sectional view of the delivery device, illustrating an example outer plunger in a proximal position and an example inner plunger in a proximal position, according to some embodiments.
Figure 13B:
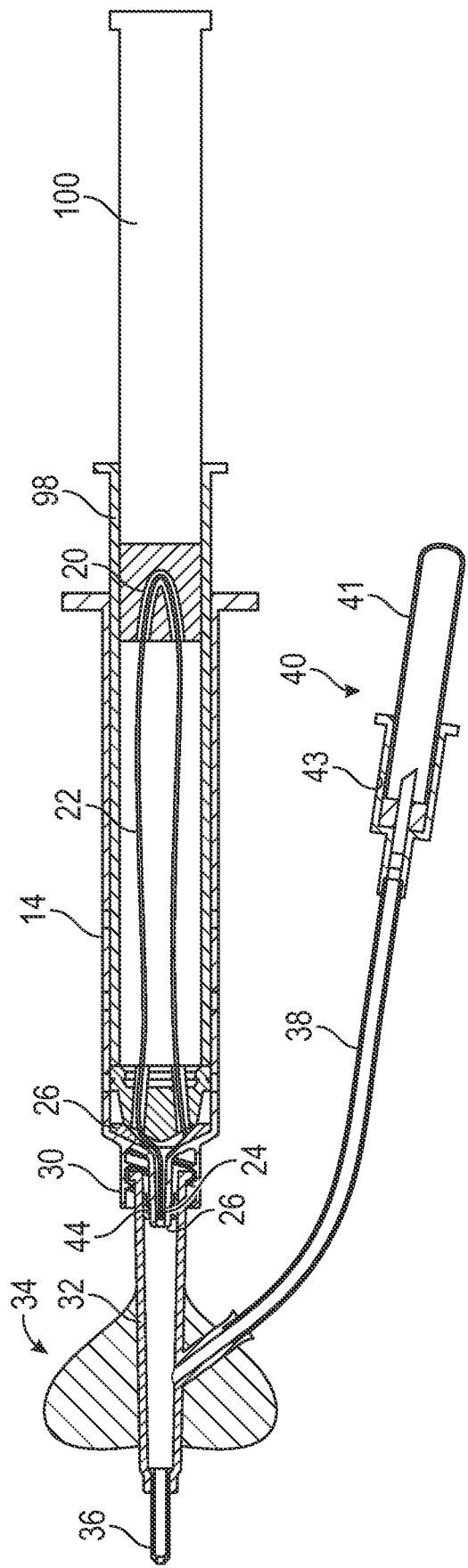
FIG. 13B is a cross-sectional view of the delivery device, illustrating the inner plunger in the proximal position after being in a distal position, and the outer barrel in a distal position, according to some embodiments.

Referring now to FIGS. 13A-13B, in some embodiments, the syringe 12 may include an outer plunger 98 and an inner plunger 100, which may be disposed within the outer plunger 98 and movable in the proximal direction and the distal direction with respect to the outer plunger 98. In some embodiments, the outer plunger 98 may be disposed within the barrel 14 and movable in the proximal direction and the distal direction with respect to the barrel 14. In some embodiments, the plunger 16 may be coupled to a distal end of the outer barrel 98. In some embodiments, the channel 20 may be disposed in a distal end of the inner barrel 100.

In some embodiments, as illustrated, for example, in FIG. 13A, the outer plunger 98 and the inner plunger 100 may be disposed in a proximal position. In some embodiments, the outer plunger 98 and the inner plunger 100 may be simultaneously advanced in the distal direction from the proximal position. In response to the outer plunger 98 and the inner plunger 100 being simultaneously advanced in the distal direction, the guidewire 22 and the stopper 18 may be advanced distally. In some embodiments, the stopper 18 may be proximate the distal end of the inner barrel 100. In some embodiments, blood collection may occur after the outer plunger 98 and the inner plunger 100 are simultaneously advanced in the distal direction. In some embodiments, in response to blood collection being complete, the inner plunger 100 may be retracted in the proximal direction, and the outer plunger 98 may remain in place, as illustrated, for example, in FIG. 13B. In some embodiments, the stopper 18 disposed within the distal end of the barrel 14 may prevent blood from entering the syringe 12.

Figure 14:
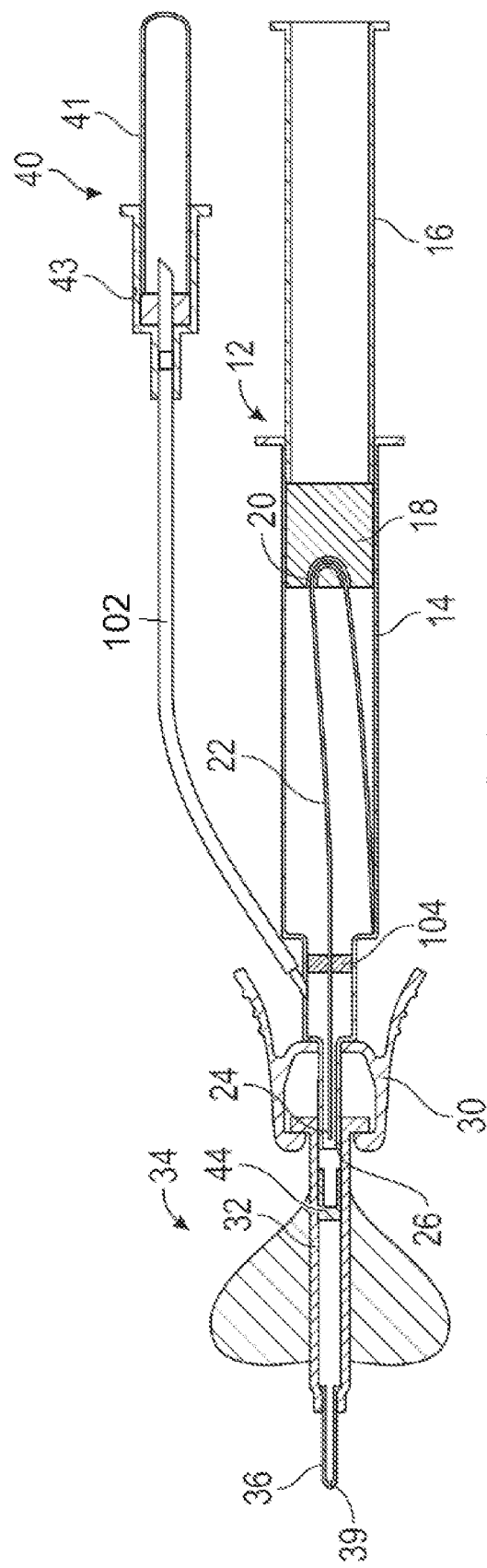
FIG. 14 is a cross-sectional view of the delivery device, according to some embodiments.

Referring now to FIG. 14, in some embodiments, an extension tube 102 may extend from the barrel 14, the distal connector 30, or another portion of the syringe 12. In some embodiments, a proximal end of the extension tube 102 may be coupled to the blood collection device. In some embodiments, a septum 104 may be disposed between the extension tube 102 and a proximal portion of the barrel 14. In some embodiments, the guidewire 22 may extend through the septum 104.

In some embodiments, the clinician may collect a blood sample from the patient by inserting a catheter (see, for example, catheter 36 of FIGS. 1A-2B) into the vasculature and pulling the plunger 16 in the proximal direction. In some embodiments, the clinician may draw blood through the extension tube 38 (see, for example, FIGS. 1A-2B) or the extension tube 102.

Figure 15A:
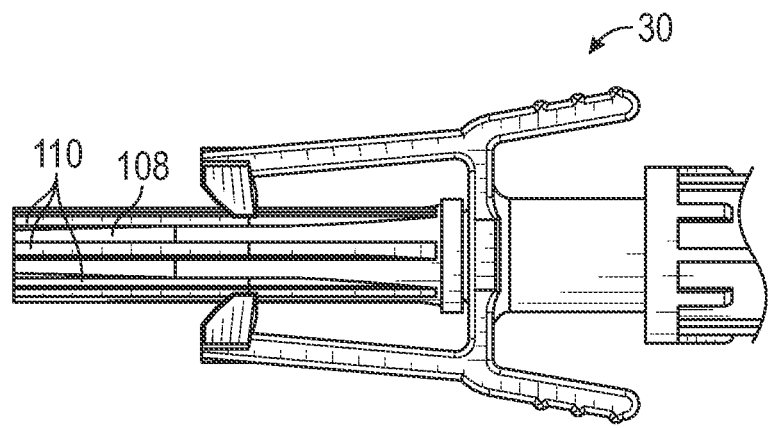
FIG. 15A is an upper perspective view of an example cap disposed on an example blunt cannula, according to some embodiments.
Figure 15B:
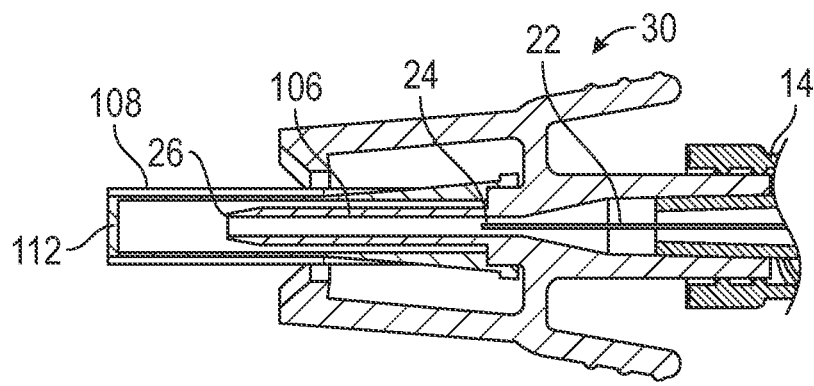
FIG. 15B is a cross-sectional view of the cap disposed on the blunt cannula, according to some embodiments.
Figure 15C:
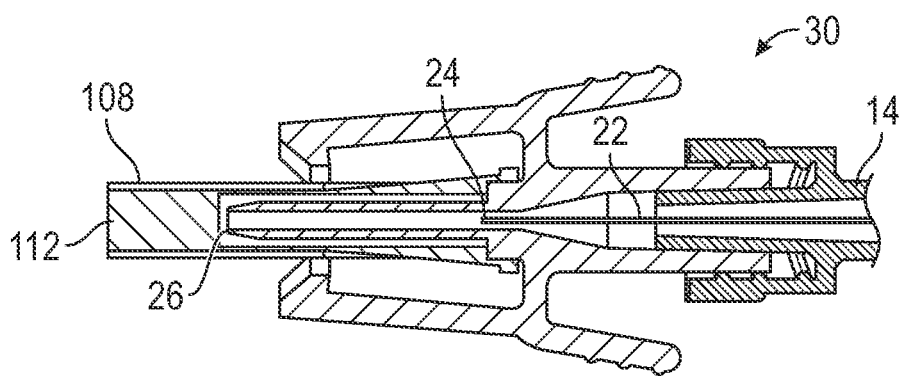
FIG. 15C is a cross-sectional view of the cap disposed on the blunt cannula, according to some embodiments.

Referring now to FIGS. 15A-15C, in some embodiments, a blunt cannula 106 of the connector 30 may form the distal opening 26. In some embodiments, a cap 108 may surround the blunt cannula 106. In some embodiments, the cap 108 may include one or more protrusions 110, which may facilitate gripping of the cap 108 by the clinician prior to removal of the cap 108 from the blunt cannula 106 by the clinician. In some embodiments, as illustrated, for example, in FIG. 15B, a distal end 112 of the cap 108 may be closed, which may prevent the guidewire 22 from moving distal to the blunt cannula 106 during shipping and/or priming. In some embodiments, the cap 108 may include one or more vent holes extending through the cap 108 proximal to the distal end 112.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A delivery device to deliver a guidewire into a catheter assembly, the delivery device comprising:
a syringe, comprising a barrel and a plunger movable within the barrel, wherein the plunger comprises a handle and a stopper coupled to a distal end of the handle, wherein the stopper comprises a channel; and
a guidewire disposed within the barrel and extending through the channel, wherein in response to depression of the plunger, the guidewire moves through the channel and a first end of the guidewire is advanced in the distal direction, wherein a second end of the guidewire is fixed, wherein the barrel contains a liquid, wherein in response to the depression of the plunger, the liquid exits a distal opening of the syringe, wherein a diameter of the distal opening of the syringe is greater than an outer diameter of the guidewire.

2. A delivery device to deliver a guidewire into a catheter assembly, the delivery device comprising:
a syringe, comprising a barrel and a plunger movable within the barrel, wherein the plunger comprises a handle and a stopper coupled to a distal end of the handle, wherein the stopper comprises a channel; and
a guidewire disposed within the barrel and extending through the channel, wherein in response to depression of the plunger, the guidewire moves through the channel and a first end of the guidewire is advanced in the distal direction, wherein a second end of the guidewire is fixed, wherein air is disposed within the barrel, wherein the barrel comprises a plurality of vent holes, wherein in response to the depression of the plunger, the air exits the vent holes.

3. A delivery device to deliver a guidewire into a catheter assembly, the delivery device comprising:
a syringe, comprising a barrel and a plunger movable within the barrel, wherein the plunger comprises a handle and a stopper coupled to a distal end of the handle, wherein the stopper comprises a channel; and
a guidewire disposed within the barrel and extending through the channel, wherein in response to depression of the plunger, the guidewire moves through the channel and a first end of the guidewire is advanced in the distal direction, wherein a second end of the guidewire is fixed, wherein in response to the depression of the plunger, the stopper is moved in the distal direction a first distance, and the first end of the guidewire is advanced in the distal direction a second distance, wherein the second distance is greater than the first distance.

4. A delivery device to deliver a guidewire into a catheter assembly, the delivery device comprising:
a syringe, comprising a barrel and a plunger movable within the barrel, wherein the plunger comprises a handle and a stopper coupled to a distal end of the handle, wherein the stopper comprises a channel; and
a guidewire disposed within the barrel and extending through the channel, wherein in response to depression of the plunger, the guidewire moves through the channel and a first end of the guidewire is advanced in the distal direction, wherein a second end of the guidewire is fixed, wherein the barrel contains a liquid, wherein the syringe further comprises a flexible housing disposed within the barrel, wherein the flexible housing prevents contact between the liquid and at least a portion of the guidewire, wherein the portion of the guidewire is surrounded by the flexible housing, wherein the housing is configured to compress in response to the plunger being depressed.

5. A delivery device to deliver a guidewire into a catheter assembly, the delivery device comprising:
a syringe, comprising a barrel and a plunger movable within the barrel, wherein the plunger comprises a handle and a stopper coupled to a distal end of the handle, wherein the stopper comprises a channel; and
a guidewire disposed within the barrel and extending through the channel, wherein in response to depression of the plunger, the guidewire moves through the channel and a first end of the guidewire is advanced in the distal direction, wherein a second end of the guidewire is fixed, wherein the syringe further comprises a biasing member disposed within the barrel distal to the stopper, wherein the biasing member is compressed in response to depression of the plunger.

6. A delivery device to deliver a guidewire into a catheter assembly, the delivery device comprising:
a syringe, comprising a barrel and a plunger movable within the barrel, wherein the plunger comprises a handle and a stopper coupled to a distal end of the handle, wherein the stopper comprises a channel; and
a guidewire disposed within the barrel and extending through the channel, wherein in response to depression of the plunger, the guidewire moves through the channel and a first end of the guidewire is advanced in the distal direction, wherein a second end of the guidewire is fixed, wherein the syringe further comprises a biasing member disposed between the stopper and the handle, wherein the biasing member expands in response to retraction of the handle.

7. A delivery device to deliver a guidewire into a catheter assembly, the delivery device comprising:
a syringe, comprising a barrel and a plunger movable within the barrel, wherein the plunger comprises a handle and a stopper coupled to a distal end of the handle, wherein the stopper comprises a channel;
a guidewire disposed within the barrel and extending through the channel, wherein in response to depression of the plunger, the guidewire moves through the channel and a first end of the guidewire is advanced in the distal direction, wherein a second end of the guidewire is fixed; and
a housing coupled to the distal end of the syringe, wherein the housing comprises saline, wherein an entirety of the guidewire is disposed proximal to the housing.

8. A delivery device to deliver a guidewire into a catheter assembly, the delivery device comprising:
a syringe, comprising a barrel and a plunger movable within the barrel, wherein the plunger comprises a handle and a stopper coupled to a distal end of the handle, wherein the stopper comprises a channel; and
a guidewire disposed within the barrel and extending through the channel, wherein in response to depression of the plunger, the guidewire moves through the channel and a first end of the guidewire is advanced in the distal direction, wherein a second end of the guidewire is fixed, wherein the guidewire forms one or more loops.

9. A delivery device to deliver a guidewire into a catheter assembly, the delivery device comprising:
a syringe, comprising a barrel and a plunger movable within the barrel, wherein the plunger comprises a handle and a stopper disposed at a distal end of the handle, wherein the syringe further comprises a channel, wherein a U-shaped portion of the channel is disposed within the handle, wherein another portion of the channel extends through the stopper; and
a guidewire disposed within the barrel and extending through the channel, wherein in response to depression of the handle in a distal direction, the stopper moves in a distal direction to a distal position, the guidewire moves through the channel, and a first end of the guidewire is advanced in the distal direction, wherein a second end of the guidewire is fixed, wherein in response to retraction of the handle in a proximal direction, the stopper remains in the distal position, the guidewire moves through the channel, and a first end of the guidewire is retracted in the proximal direction.

10. The delivery device of claim 9, wherein the barrel contains a liquid, wherein in response to the depression of the plunger, the liquid exits a distal opening of the syringe, wherein a diameter of the distal opening of the syringe is greater than an outer diameter of the guidewire.

11. The delivery device of claim 9, wherein air is disposed within the barrel, wherein the barrel comprises a plurality of vent holes, wherein in response to the depression of the plunger, the air exits the vent holes.

12. The delivery device of claim 9, wherein in response to the depression of the plunger, the stopper is moved in the distal direction a first distance, and the first end of the guidewire is advanced in the distal direction a second distance, wherein the second distance is greater than the first distance.

13. The delivery device of claim 9, wherein the barrel contains a liquid, wherein the syringe further comprises a flexible housing disposed within the barrel, wherein the flexible housing prevents contact between the liquid and at least a portion of the guidewire, wherein the portion of the guidewire is surrounded by the flexible housing, wherein the housing is configured to compress in response to the plunger being depressed.

14. The delivery device of claim 9, wherein the syringe further comprises a biasing member disposed within the barrel distal to the stopper, wherein the biasing member is compressed in response to depression of the plunger.

15. The delivery device of claim 9, wherein the syringe further comprises a biasing member disposed between the U-shaped portion and the handle, wherein the biasing member expands in response to retraction of the handle in the proximal direction.

16. A delivery device for delivering a guidewire into a catheter assembly, the delivery device comprising:
 a first syringe, comprising a first barrel and a first plunger movable within the first barrel, wherein the first plunger comprises a first handle and a first stopper coupled to a distal end of the first handle, wherein the first stopper comprises a channel, wherein air is disposed within the first barrel, wherein the first barrel comprises a plurality of vent holes, wherein in response to the depression of the first plunger, the air exits the vent holes;
 a guidewire disposed within the first barrel and extending through the channel, wherein in response to depression of the first plunger, the first guidewire moves through the channel, and a first end of the guidewire is advanced in the distal direction, wherein a second end of the guidewire is fixed;
 a second syringe, comprising a second barrel and a second plunger movable within the second barrel, wherein the second plunger comprises a second handle and a second stopper coupled to a distal end of the second handle, wherein the second barrel contains a liquid, wherein in response to the depression of the second plunger, the liquid exits a distal opening of the second syringe; and
 an adapter comprising a first port, a second port, and a third port, wherein the first port is coupled to a distal end of the first syringe, wherein the second port is coupled to a distal end of the second syringe, wherein the third port is configured to couple to the catheter assembly.

17. The delivery device of claim 16, wherein the first barrel and the second barrel are integrally formed.

18. The delivery device of claim 16, wherein the first plunger is coupled to the second plunger.

19. The delivery device of claim 16, wherein the first port is integrally formed with the first syringe or the second port is integrally formed with the second port.

* * * * *